(12) United States Patent
Ghosh et al.

(10) Patent No.: US 11,471,678 B2
(45) Date of Patent: Oct. 18, 2022

(54) CARDIAC CYCLE SELECTION

(71) Applicant: Medtronic, Inc., Minneapolis, MN (US)

(72) Inventors: Subham Ghosh, Blaine, MN (US); D'Anne E. Kudlik, Lino Lakes, MN (US); Karen J. Kleckner, Blaine, MN (US); Melissa M. Rhodes, Columbia Heights, MN (US); Keelia Doyle, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 632 days.

(21) Appl. No.: 16/047,619

(22) Filed: Jul. 27, 2018

(65) Prior Publication Data
US 2019/0030331 A1 Jan. 31, 2019

Related U.S. Application Data

(60) Provisional application No. 62/538,337, filed on Jul. 28, 2017.

(51) Int. Cl.
*A61B 5/318* (2021.01)
*A61N 1/36* (2006.01)
(Continued)

(52) U.S. Cl.
CPC ............ *A61N 1/3603* (2017.08); *A61B 5/282* (2021.01); *A61B 5/287* (2021.01); *A61B 5/352* (2021.01); *A61B 5/366* (2021.01); *A61B 5/4836* (2013.01); *A61N 1/321* (2013.01); *A61N 1/3627* (2013.01); *A61N 1/3682* (2013.01); *A61N 1/3684* (2013.01); *A61N 1/36507* (2013.01); *A61B 5/25* (2021.01); *A61B 5/316* (2021.01);
(Continued)

(58) Field of Classification Search
CPC ... A61B 5/0452; A61B 5/0456; A61B 5/0468; A61B 5/0472
See application file for complete search history.

(56) References Cited

U.S. PATENT DOCUMENTS 4,233,987 A 11/1980 Feingold
4,402,323 A 9/1983 White
(Continued)

FOREIGN PATENT DOCUMENTS

CN 1043621 A 7/1990
CN 1253761 A 5/2000
(Continued)

OTHER PUBLICATIONS

International Search Report and Written Opinion dated Oct. 23, 2018 for International Application No. PCT/US2018/043930; 11 pages.
(Continued)

*Primary Examiner* — Allen Porter
(74) *Attorney, Agent, or Firm* — Mueting Raasch Group

(57) ABSTRACT

Systems and methods are described herein for selection of a cardiac cycle, or heartbeat, from a plurality of cardiac cycles monitored over time. The cardiac cycle may be selected using various metrics including a single-cycle metric and a cycle-series metric. Further, the selected cardiac cycle may be used for further cardiac analysis (for example, to generate electrical activation times).

31 Claims, 14 Drawing Sheets

(51) Int. Cl.

| | | |
|---|---|---|
| *A61B 5/00* | (2006.01) | |
| *A61N 1/362* | (2006.01) | |
| *A61N 1/365* | (2006.01) | |
| *A61B 5/282* | (2021.01) | |
| *A61B 5/287* | (2021.01) | |
| *A61B 5/352* | (2021.01) | |
| *A61B 5/366* | (2021.01) | |
| *A61N 1/32* | (2006.01) | |
| *A61N 1/368* | (2006.01) | |
| *A61B 5/25* | (2021.01) | |
| *A61B 5/316* | (2021.01) | |
| *A61B 5/363* | (2021.01) | |
| *A61B 5/364* | (2021.01) | |
| *A61N 1/39* | (2006.01) | |

(52) U.S. Cl.
CPC ............... *A61B 5/363* (2021.01); *A61B 5/364* (2021.01); *A61B 5/6805* (2013.01); *A61B 5/686* (2013.01); *A61B 5/6831* (2013.01); *A61B 5/7203* (2013.01); *A61B 5/7275* (2013.01); *A61N 1/3622* (2013.01); *A61N 1/3686* (2013.01); *A61N 1/36843* (2017.08); *A61N 1/3925* (2013.01)

(56) References Cited

U.S. PATENT DOCUMENTS

| | | | |
|---|---|---|---|
| 4,428,378 A | 1/1984 | Anderson et al. | |
| 4,497,326 A | 2/1985 | Curry | |
| 4,566,456 A | 1/1986 | Koning et al. | |
| 4,593,702 A | 6/1986 | Kepski | |
| 4,674,511 A | 6/1987 | Cartmell | |
| 4,763,660 A | 8/1988 | Kroll et al. | |
| 4,777,955 A | 10/1988 | Brayten et al. | |
| 4,787,389 A | 11/1988 | Tarjan | |
| 4,979,507 A | 12/1990 | Heinz et al. | |
| 5,052,388 A | 10/1991 | Sivula et al. | |
| 5,054,496 A | 10/1991 | Wen et al. | |
| 5,311,873 A | 5/1994 | Savard et al. | |
| 5,331,960 A | 7/1994 | Lavine | |
| 5,334,220 A | 8/1994 | Sholder | |
| 5,443,492 A | 8/1995 | Stokes et al. | |
| 5,485,849 A | 1/1996 | Panescu et al. | |
| 5,514,163 A | 5/1996 | Markowitz et al. | |
| 5,552,645 A | 9/1996 | Weng | |
| 5,628,778 A | 5/1997 | Kruse et al. | |
| 5,671,752 A | 9/1997 | Sinderby et al. | |
| 5,683,429 A | 11/1997 | Mehra | |
| 5,683,432 A | 11/1997 | Goedeke et al. | |
| 5,687,737 A | 11/1997 | Branham et al. | |
| 5,810,740 A | 9/1998 | Paisner | |
| 5,876,336 A | 3/1999 | Swanson et al. | |
| 5,891,045 A | 4/1999 | Albrecht et al. | |
| 5,922,014 A | 7/1999 | Warman et al. | |
| 6,055,448 A | 4/2000 | Anderson et al. | |
| 6,128,535 A | 10/2000 | Maarse et al. | |
| 6,141,588 A | 10/2000 | Cox et al. | |
| 6,187,032 B1 | 2/2001 | Ohyu et al. | |
| 6,205,357 B1 | 3/2001 | Ideker et al. | |
| 6,226,542 B1 | 5/2001 | Reisfeld | |
| 6,236,883 B1 | 5/2001 | Ciaccio et al. | |
| 6,243,603 B1 | 6/2001 | Ideker et al. | |
| 6,246,898 B1 | 6/2001 | Vesely et al. | |
| 6,301,496 B1 | 10/2001 | Reisfeld | |
| 6,311,089 B1 | 10/2001 | Mann et al. | |
| 6,330,476 B1 | 12/2001 | Ben-Haim et al. | |
| 6,358,214 B1 | 3/2002 | Tereschouk | |
| 6,377,856 B1 | 4/2002 | Carson | |
| 6,381,493 B1 | 4/2002 | Stadler et al. | |
| 6,393,316 B1 | 5/2002 | Gillberg et al. | |
| 6,418,346 B1 | 7/2002 | Nelson et al. | |
| 6,442,433 B1 | 8/2002 | Linberg | |
| 6,456,867 B2 | 9/2002 | Reisfeld | |
| 6,473,638 B2 | 10/2002 | Ferek-Petric | |
| 6,480,745 B2 | 11/2002 | Nelson et al. | |
| 6,484,118 B1 | 11/2002 | Govari | |
| 6,507,756 B1 | 1/2003 | Heynen et al. | |
| 6,532,379 B2 | 3/2003 | Stratbucker | |
| 6,584,343 B1 | 6/2003 | Ransbury et al. | |
| 6,599,250 B2 | 7/2003 | Webb et al. | |
| 6,625,482 B1 | 9/2003 | Panescu et al. | |
| 6,640,136 B1 | 10/2003 | Helland et al. | |
| 6,650,927 B1 | 11/2003 | Keidar | |
| 6,766,189 B2 | 7/2004 | Yu et al. | |
| 6,772,004 B2 | 8/2004 | Rudy | |
| 6,804,555 B2 | 10/2004 | Warkentin | |
| 6,847,836 B1 | 1/2005 | Sujdak | |
| 6,856,830 B2 | 2/2005 | He | |
| 6,882,882 B2 | 4/2005 | Struble et al. | |
| 6,885,889 B2 | 4/2005 | Chinchoy | |
| 6,915,149 B2 | 7/2005 | Ben-Haim | |
| 6,968,237 B2 | 11/2005 | Doan et al. | |
| 6,975,900 B2 | 12/2005 | Rudy et al. | |
| 6,978,184 B1 | 12/2005 | Marcus et al. | |
| 6,980,675 B2 | 12/2005 | Evron et al. | |
| 7,016,719 B2 | 3/2006 | Rudy et al. | |
| 7,031,777 B2 | 4/2006 | Hine et al. | |
| 7,058,443 B2 | 6/2006 | Struble | |
| 7,062,315 B2 | 6/2006 | Koyrakh et al. | |
| 7,092,759 B2 | 8/2006 | Nehls et al. | |
| 7,142,922 B2 | 11/2006 | Spinelli et al. | |
| 7,184,835 B2 | 2/2007 | Kramer et al. | |
| 7,215,998 B2 | 5/2007 | Wesselink et al. | |
| 7,238,158 B2 | 7/2007 | Abend | |
| 7,286,866 B2 | 10/2007 | Okerlund et al. | |
| 7,308,297 B2 | 12/2007 | Reddy et al. | |
| 7,308,299 B2 | 12/2007 | Burrell et al. | |
| 7,313,444 B2 | 12/2007 | Pianca et al. | |
| 7,321,677 B2 | 1/2008 | Evron et al. | |
| 7,346,381 B2 | 3/2008 | Okerlund et al. | |
| 7,398,116 B2 | 7/2008 | Edwards | |
| 7,426,412 B1 | 9/2008 | Schecter | |
| 7,454,248 B2 | 11/2008 | Burrell et al. | |
| 7,499,743 B2 | 3/2009 | Vass et al. | |
| 7,509,170 B2 | 3/2009 | Zhang et al. | |
| 7,565,190 B2 | 7/2009 | Okerlund et al. | |
| 7,587,074 B2 | 9/2009 | Zarkh et al. | |
| 7,599,730 B2 | 10/2009 | Hunter et al. | |
| 7,610,088 B2 | 10/2009 | Chinchoy | |
| 7,613,500 B2 | 11/2009 | Vass et al. | |
| 7,616,993 B2 | 11/2009 | Müssig et al. | |
| 7,664,550 B2 | 2/2010 | Eick et al. | |
| 7,684,863 B2 | 3/2010 | Parikh et al. | |
| 7,742,629 B2 | 6/2010 | Zarkh et al. | |
| 7,747,047 B2 | 6/2010 | Okerlund et al. | |
| 7,751,882 B1 | 7/2010 | Helland et al. | |
| 7,769,451 B2 | 8/2010 | Yang et al. | |
| 7,778,685 B2 | 8/2010 | Evron et al. | |
| 7,778,686 B2 | 8/2010 | Vass et al. | |
| 7,787,951 B1 | 8/2010 | Min | |
| 7,813,785 B2 | 10/2010 | Okerlund et al. | |
| 7,818,040 B2 | 10/2010 | Spear et al. | |
| 7,848,807 B2 | 12/2010 | Wang | |
| 7,860,580 B2 | 12/2010 | Falk et al. | |
| 7,894,889 B2 | 2/2011 | Zhang | |
| 7,912,544 B1 | 3/2011 | Min et al. | |
| 7,917,214 B1 | 3/2011 | Gill et al. | |
| 7,941,213 B2 | 5/2011 | Markowitz et al. | |
| 7,953,475 B2 | 5/2011 | Harlev et al. | |
| 7,953,482 B2 | 5/2011 | Hess | |
| 7,983,743 B2 | 7/2011 | Rudy et al. | |
| 7,996,063 B2 | 8/2011 | Vass et al. | |
| 7,996,070 B2 | 8/2011 | van Dam et al. | |
| 8,010,194 B2 | 8/2011 | Muller | |
| 8,019,402 B1 | 9/2011 | Kryzpow et al. | |
| 8,019,409 B2 | 9/2011 | Rosenberg et al. | |
| 8,032,229 B2 | 10/2011 | Gerber et al. | |
| 8,036,743 B2 | 10/2011 | Savage et al. | |
| 8,060,185 B2 | 11/2011 | Hunter et al. | |
| 8,150,513 B2 | 4/2012 | Chinchoy | |
| 8,160,700 B1 | 4/2012 | Ryu et al. | |
| 8,175,703 B2 | 5/2012 | Dong et al. | |

(56) References Cited

U.S. PATENT DOCUMENTS

| | | |
|---|---|---|
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,731,642 B2 | 5/2014 | Zarkh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,861,830 B2 | 10/2014 | Brada et al. |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 9,789,319 B2 | 10/2017 | Sambelashvili |
| 9,924,884 B2 | 3/2018 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0010201 A1* | 1/2004 | Korzinov .......... A61B 5/04325 600/518 |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0167809 A1 | 7/2007 | Dala-Krishna |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143692 A1 | 6/2009 | Brockway et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |

(56) References Cited

U.S. PATENT DOCUMENTS

| | | |
|---|---|---|
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Ghosh |
| 2016/0331258 A1 | 11/2016 | Du et al. |
| 2017/0246460 A1 | 8/2017 | Ghosh |
| 2017/0246461 A1 | 8/2017 | Ghosh |
| 2017/0143976 A1 | 11/2017 | Tazawa et al. |
| 2018/0263522 A1 | 9/2018 | Ghosh et al. |
| 2018/0264258 A1 | 9/2018 | Cheng et al. |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A1 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 S1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/009563 A1 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | 2014/179459 A3 | 1/2015 |
| WO | 2015/013271 A1 | 1/2015 |
| WO | 2015/013493 A1 | 1/2015 |
| WO | 2015/013574 A1 | 1/2015 |

OTHER PUBLICATIONS

International Search Report and Written Opinion dated May 3, 2012 for International Application No. PCT/US2012/036262; 9 pages.
International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.

(56) References Cited

OTHER PUBLICATIONS

International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," Circulation, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Nonischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete I11-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, 2011, September; 8(9): 1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST—Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Lumason™, Brochure, Bracco Diagnostocs. Oct. 2014.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

(56) References Cited

OTHER PUBLICATIONS

Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.

Steinhaus BM., "Estimating cardiac transmembrane activation and recovery times from unipolar and bipolar extracellular electrograms: a simulation study," Circulation Research, 1989, 64:449-462.

Strik et al., "Electrical and Mechanical Ventricular Activation During Left Bundle Branch Block and Resynchronization," *J of Cardiovasc. Trans. Res.*, 2012; 5:117-126.

Svendsen et al., "Computational Models of Cardiac Electrical Activation," Chapter 5, Computational Nov. 2010, pp. 73-88.

Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-34. Available online Jan. 25, 2010.

Sweeney et al., QRS Fusion Complex Analysis Using Wave Interference to Predict Reverse Remodeling During Cardiac Resynchronization Therapy, heart Rhythm, 2014, 11:806-813.

Turner et al, "Electrical and Mechanical Components of Dyssynchrony in Heart Failure Patients with Normal QRS Duration and Left Bundle-Branch Block," *Circulation* 2004; 109:2544-2549.

Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Wang et al., "Application of the Method of Fundamental Solutions to Potential-based Inverse Electrocardiography," Annals of Biomedical Engineering, Aug. 2006, pp. 1272-1288.

Wellens, MD et al., "The Electrocardiogram 102 Years After Einthoven," Circulation, Feb. 2004; vol. 109, No. 5, pp. 562-564.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

\* cited by examiner

FIG. 8

| Metric | Beat 1 | Beat 2 | Beat 3 | Beat 4 | Beat 5 |
|---|---|---|---|---|---|
| $M_{max}$ | Value = 0.98 | Value = 1 | Value = 0.93 | Value = 1.33 | Value = 1.05 |
| $M_{min}$ | Value = 1 | Value = 1 | Value = 1.50 | Value = 4.63 | Value = 0.38 |
| $M_{sum}$ | Value = 0.99 | Value = 1 | Value = 0.95 | Value = 1.02 | Value = 1.07 |
| $M_{rr}$ | Value = 1 | Value = 1 | Value = 1 | Value = 0.70 | Value = 1.09 |

FIG. 9

| Metric | Beat 1 | Beat 2 | Beat 3 | Beat 4 | Beat 5 |
|---|---|---|---|---|---|
| $M_{max}$ | 0 | 0 | 0 | 1 | 0 |
| $M_{min}$ | 0 | 0 | 1 | 1 | 1 |
| $M_{sum}$ | 0 | 0 | 0 | 0 | 0 |
| $M_{rr}$ | 0 | 0 | 0 | 1 | 0 |
| Score | 0 | 0 | 1 | 3 | 1 |

CARDIAC CYCLE SELECTION

This application claims the benefit of U.S. Provisional Patent Application No. 62/538,337, filed Jul. 28, 2017, which is incorporated herein by reference in its entirety.

The disclosure herein relates to systems and methods for use in the selection of a cardiac cycle, or heartbeat, from a plurality of cardiac cycles, e.g., for use in determining one or more features of the cardiac cycle.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on the heart. In some cases, the equipment provides information to the physician about the electrical activity of the heart and the location of the intracardiac lead. The equipment may perform similar functions as the medical device, including delivering electrical stimulation to the heart and sensing the depolarizations of the heart. In some cases, the equipment may include equipment for obtaining an electrocardiogram (ECG) via electrodes on the surface, or skin, of the patient. More specifically, the patient may have a plurality of electrodes on an ECG belt or vest that surrounds the torso of the patient. After the belt or vest has been secured to the torso, a physician can perform a series of tests to evaluate a patient's cardiac response. The evaluation process can include detection of a baseline rhythm in which no electrical stimuli is delivered to cardiac tissue and another rhythm after electrical stimuli is delivered to the cardiac tissue.

The ECG electrodes placed on the body surface of the patient may be used for various therapeutic purposes (e.g., cardiac resynchronization therapy) including optimizing lead location, pacing parameters, etc. based on one or more metrics derived from the signals captured by the ECG electrodes. For example, electrical heterogeneity information may be derived from electrical activation times computed from multiple electrodes on the body surface.

Further, the signals from multiple electrodes on the body surface can be used to determine one or more specific ECG features such as, e.g., QRS onset, peak, offset, etc. for a series of multiple heartbeats. Such ECG features may be used by themselves to evaluate cardiac health and/or therapy, or may be used to calculate, or compute, electrical activation times. However, in one or more instances, only a single QRS complex is used to determine the therapeutic nature of one or more parameters related to cardiac therapy such as, e.g., pacing parameters, lead location, etc. Further, repeated measurements may have high computational and temporal costs in addition to unnecessary redundancy.

SUMMARY

The exemplary systems and methods described herein may create processes to identify irregular patterns within a QRS onset and QRS offset (e.g., premature ventricular contractions (PVCs), etc.) of a cardiac cycle and to determine which cardiac cycle, or heartbeat, is representative of the conduction pattern with the current pacing parameters. This cardiac cycle may then be identified and selected for further, more computationally-expensive metrics calculations for cardiac resynchronization therapy (CRT) optimization such as, e.g., generation of activation times, generation of electrical heterogeneity metrics, etc.

The exemplary systems and methods described herein may be configured to assist a user (e.g., a physician) in evaluating a patient without cardiac therapy being delivered to the patient (e.g., prior to IMD implant) and/or configuring cardiac therapy being delivered to a patient (e.g., cardiac therapy being performed on a patient during and/or after implantation of cardiac therapy apparatus). The systems and methods may be described as being noninvasive. For example, the systems and methods may not need implantable devices such as leads, probes, sensors, catheters, etc. to evaluate and configure the cardiac therapy. Instead, the systems and methods may use electrical measurements taken noninvasively using, e.g., a plurality of external electrodes attached to the surface, or skin, of a patient about the patient's torso.

One exemplary system for use in cardiac evaluation may include electrode apparatus and computing apparatus. The electrode apparatus may include a plurality of external electrodes to be located proximate tissue of a patient. The computing apparatus may be coupled to the electrode apparatus and configured to monitoring electrical activity using the plurality of electrodes to provide a plurality of electrical signals over a plurality of cardiac cycles. The computing apparatus may be further configured to generate at least one metric for each cardiac cycle based on a single-cycle submetric and a cycle-series submetric and select a cardiac cycle of the plurality of cardiac cycles based on the at least one metric. The single-cycle submetric may be based on at least two of the plurality of electrical signals during the cardiac cycle and the cycle-series submetric may be based on at least two of the plurality of electrical signals during at least two cardiac cycles.

One exemplary method for use in cardiac evaluation may include monitoring electrical activity from tissue of a patient using a plurality of electrodes to generate a plurality of electrical signals over a plurality of cardiac cycles, generating at least one metric for each cardiac cycle based on a single-cycle submetric and a cycle-series submetric, and selecting a cardiac cycle of the plurality of cardiac cycles based on the at least one metric. The single-cycle submetric may be based on at least two of the plurality of electrical signals during the cardiac cycle and the cycle-series submetric may be based on at least two of the plurality of electrical signals during at least two cardiac cycles.

In one or more embodiments, the single-cycle submetric may be a value generated from at least two of the plurality of electrical signals at a peak time during the cardiac cycle and the cycle-series submetric may be a value generated from at least two electrical signals of the plurality of electrical signals at peak times during the at least two cardiac cycles.

In one or more embodiments, the at least one metric for each cardiac cycle may include a maximum amplitude metric. The single-cycle submetric may be a maximum value across at least two of the plurality electrical signals at a peak time during cardiac cycle, and the cycle-series submetric may be a composite maximum value based on all of the maximum values of at least two of the plurality of electrical signals at peak times during the at least two cardiac cycles. The maximum amplitude metric may be the single-cycle submetric divided by the cycle-series submetric. Further, in one or more embodiments, the composite maximum value is the median of the maximum values of the at least two of the plurality of electrical signals at the peak times during the at least two cardiac cycles.

In one or more embodiments, the at least one metric for each cardiac cycle may include a minimum amplitude metric. The single-cycle submetric may be a minimum value across at least two of the plurality electrical signals at a peak time during cardiac cycle, and the cycle-series submetric may be a composite minimum value based on all of the minimum values of at least two of the plurality of electrical signals at peak times during the at least two cardiac cycles. The minimum amplitude metric may be the single-cycle submetric divided by the cycle-series submetric.

In one or more embodiments, the at least one metric for each cardiac cycle may include a sum amplitude metric. The single-cycle submetric may be a sum of at least two of the plurality of electrical signals at a peak time during the cardiac cycle, and the cycle-series submetric may be a composite sum value based on at least two of the plurality of electrical signals at peak times during the at least two cardiac cycles. The sum amplitude metric may be the single-cycle submetric divided by the cycle-series submetric.

In one or more embodiments, the at least one metric for each cardiac cycle may include an interval metric. The single-cycle submetric may be a time interval between a peak time of the cardiac cycle and a peak time of a previous or following cardiac cycle of the plurality of cardiac cycles, and the cycle-series submetric may be a composite interval value based on all time intervals between peak times of at least two cardiac cycles.

In one or more embodiments, the at least one metric for each cardiac cycle may include an electrode contact metric. The electrode contact metric may be representative of an amount of the plurality of electrodes that captured a valid electrocardiographic signal from the tissue of the patient during the cardiac cycle.

In one or more embodiments, the at least one metric for each cardiac cycle may include a regional electrode contact metric. The regional electrode contact metric may be representative of an amount of the plurality of electrodes located proximate a selected region of the patient that captured a valid electrocardiographic signal from the tissue in the selection region of the patient during the cardiac cycle.

In one or more embodiments, selecting a cardiac cycle of the plurality of cardiac cycles based on the at least one metric may include comparing the at least one metric for each cardiac cycle to at least one threshold value to assign a score the cardiac cycle.

In one or more embodiments, selecting a cardiac cycle of the plurality of cardiac cycles based on the at least one metric may include assigning a score to each cardiac cycle of the plurality of cardiac cycles and selecting the cardiac cycle of the plurality of cardiac cycles having the best score.

In one or more embodiments, selecting a cardiac cycle of the plurality of cardiac cycles based on the at least one metric may include assigning a score to each cardiac cycle of the plurality of cardiac cycles and removing from consideration of selection cardiac cycles of the plurality of cardiac cycles having a score greater than a scoring threshold value.

In one or more embodiments, selecting a cardiac cycle of the plurality of cardiac cycles based on the at least one metric may include removing from consideration of selection cardiac cycles of the plurality of cardiac cycles following or preceding cardiac cycles having a score greater than the scoring threshold value.

In one or more embodiments, selecting a cardiac cycle of the plurality of cardiac cycles based on the at least one metric may include removing from consideration of selection the cardiac cycle that occurs last if at least two cardiac cycles remain being considered for selection.

In one or more embodiments, the computing apparatus may be further configured to execute or the method further may include generating electrical activation times based on the plurality of cardiac signals of the selected cardiac cycle.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 8 is a table of exemplary metrics generated from a plurality of electrical signals for five cardiac cycles.

FIG. 9 is a table of scoring the five cardiac cycles of FIG. 8 according to the exemplary metrics thereof.

DETAILED DESCRIPTION OF EXEMPLARY EMBODIMENTS

Figure 1:
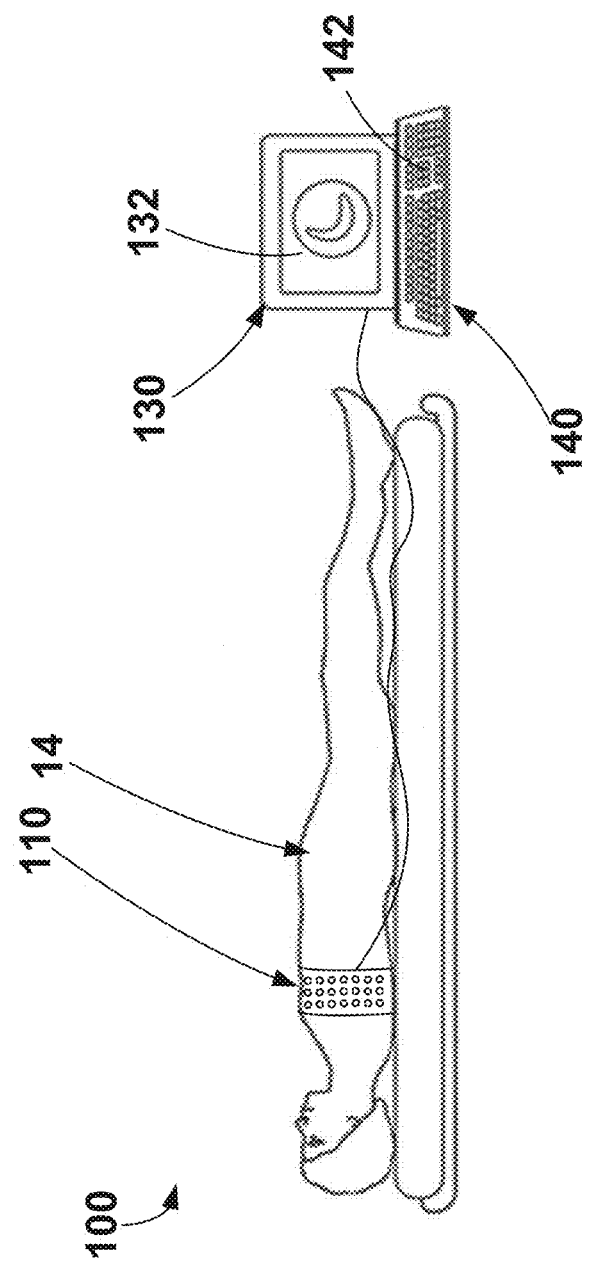
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-13. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

A plurality of electrocardiogram (ECG) recordings or signals may be measured, or monitored, using a plurality of external electrodes positioned about the surface, or skin, of a patient. The ECG signals may be used to evaluate and configured cardiac therapy such as, e.g., CRT. As described herein, the ECG signals may be gathered or obtained noninvasively since, e.g., implantable electrodes may not be used to measure the ECG signals. Further, the ECG signals may be used to determine cardiac electrical activation times, which may be used to generate various metrics (e.g., electrical heterogeneity information) that may be used by a user (e.g., physician) to optimize one or more settings, or parameters, of pacing therapy.

Various exemplary systems and methods may be configured to use electrode apparatus including external electrodes, display apparatus, and computing apparatus to noninvasively assist a user (e.g., a physician) in the evaluation of cardiac health and/or the configuration (e.g., optimization) of cardiac therapy. An exemplary system 100 including electrode apparatus 110, display apparatus 130, and computing apparatus 140 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems and methods described herein may further use imaging apparatus to provide noninvasive assistance to a user (e.g., a physician) to locate, or select, a pacing electrode or vector proximate the patient's heart in conjunction with the configuration of cardiac therapy.

For example, the exemplary systems and methods may provide image guided navigation that may be used to navigate leads including electrodes, leadless electrodes, wireless electrodes, catheters, etc., within the patient's body while also providing noninvasive cardiac therapy configuration including determining an effective, or optimal, A-V interval. Exemplary systems and methods that use imaging apparatus and/or electrode apparatus may be described in U.S. Pat. App. Pub. No. 2014/0371832 to Ghosh published on Dec. 18, 2014, U.S. Pat. App. Pub. No. 2014/0371833 to Ghosh et al. published on Dec. 18, 2014, U.S. Pat. App. Pub. No. 2014/0323892 to Ghosh et al. published on Oct. 30, 2014, U.S. Pat. App. Pub. No. 2014/0323882 to Ghosh et al. published on Oct. 20, 2014, each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate implantable apparatus to target locations within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 to Zarkh et al. issued on May 20, 2014, U.S. Pat. No. 8,861,830 to Brada et al. issued on Oct. 14, 2014, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat.

No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the therapeutic nature of one or more parameters related to cardiac therapy such as, e.g., pacing parameters, lead location, etc. More specifically, for example, the QRS complex of a single cardiac cycle may be evaluated for one or more metrics such as, e.g., QRS onset, QRS offset, QRS peak, electrical heterogeneity information, electrical activation times, left ventricular or thoracic standard deviation of electrical activation times (LVED), standard deviation of activation-times (SDAT), average left ventricular or thoracic surrogate electrical activation times (LVAT), referenced to earliest activation time, QRS duration (e.g., interval between QRS onset to QRS offset), difference between average left surrogate and average right surrogate activation times, relative or absolute QRS morphology, difference between a higher percentile and a lower percentile of activation times (higher percentile may be 90%, 80%, 75%, 70%, etc. and lower percentile may be 10%, 15% 20%, 25% and 30%, etc.), other statistical measures of central tendency (e.g. median or mode), dispersion (e.g. mean deviation, standard deviation, variance, interquartile deviations, range) applied to all activation times or right or left surrogate activation times, etc. However, in one or more instances, only a single cardiac cycle (e.g., a single QRS complex) may be used for evaluation. Thus, the display apparatus 130 and the computing apparatus 140 may be configured to analyze the electrical signals (ECG) over a plurality of cardiac cycles, or heartbeats, using the plurality of signals resulting in a plurality of electrical signals over a plurality of cardiac cycles, and then select a single cardiac cycle for further evaluation from the plurality of cardiac cycles. In this way, irregular or anomalous cardiac cycles or other cardiac cycles having undesirable characteristics may be discarded while a more desirable cardiac cycle is selected for evaluation. It is to be understood that a more desirable cardiac cycle does not necessarily mean that the most "healthy" cardiac cycle is selected. Instead, a cardiac cycle having the desired signal characteristics for use in proper evaluation may be the cardiac cycle selected. Further, as described herein, the QRS complex of the electrical signal of the cardiac cycle may be the specific portion of the electrical signal corresponding to the cardiac cycle selected.

In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for analyzing a plurality of electrical signals captured by the electrode apparatus 110, for determining QRS onsets, QRS offsets, medians, modes, averages, peaks or maximum values, valleys or minimum values, for determining electrical activation times, for selecting a heartbeat or QRS complex based on one or more metrics or tests, for scoring heartbeats and QRS complexes based on one or more metrics or features of the heartbeats and QRS complexes, for driving a graphical user interface configured to noninvasively assist a user in configuring one or more pacing parameters, or settings, such as, e.g., A-V interval, V-V interval, for driving a graphical user interface configured to noninvasively assist a user in selecting a pacing location before, during, or after implantation of an implantable medical device, etc.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to view and/or select one or more pieces of configuration information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including one or more heartbeats, QRS complexes, pacing parameters, electrical heterogeneity information, textual instructions, graphical depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110 (e.g., a plurality of QRS complexes), electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be necessary for carrying out the one and/or more processes or methods described herein.

In one or more embodiments, the exemplary systems and methods may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems and methods interfaces may be implemented using a computer readable storage medium, configured with a computer program, where the storage medium so configured causes the computer to operate in a specific and predefined manner to perform functions described herein. Further, in at least one embodiment, the exemplary systems and methods may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, mini computer, tablet computer, etc.). The exact configuration of the computing apparatus 140 is not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
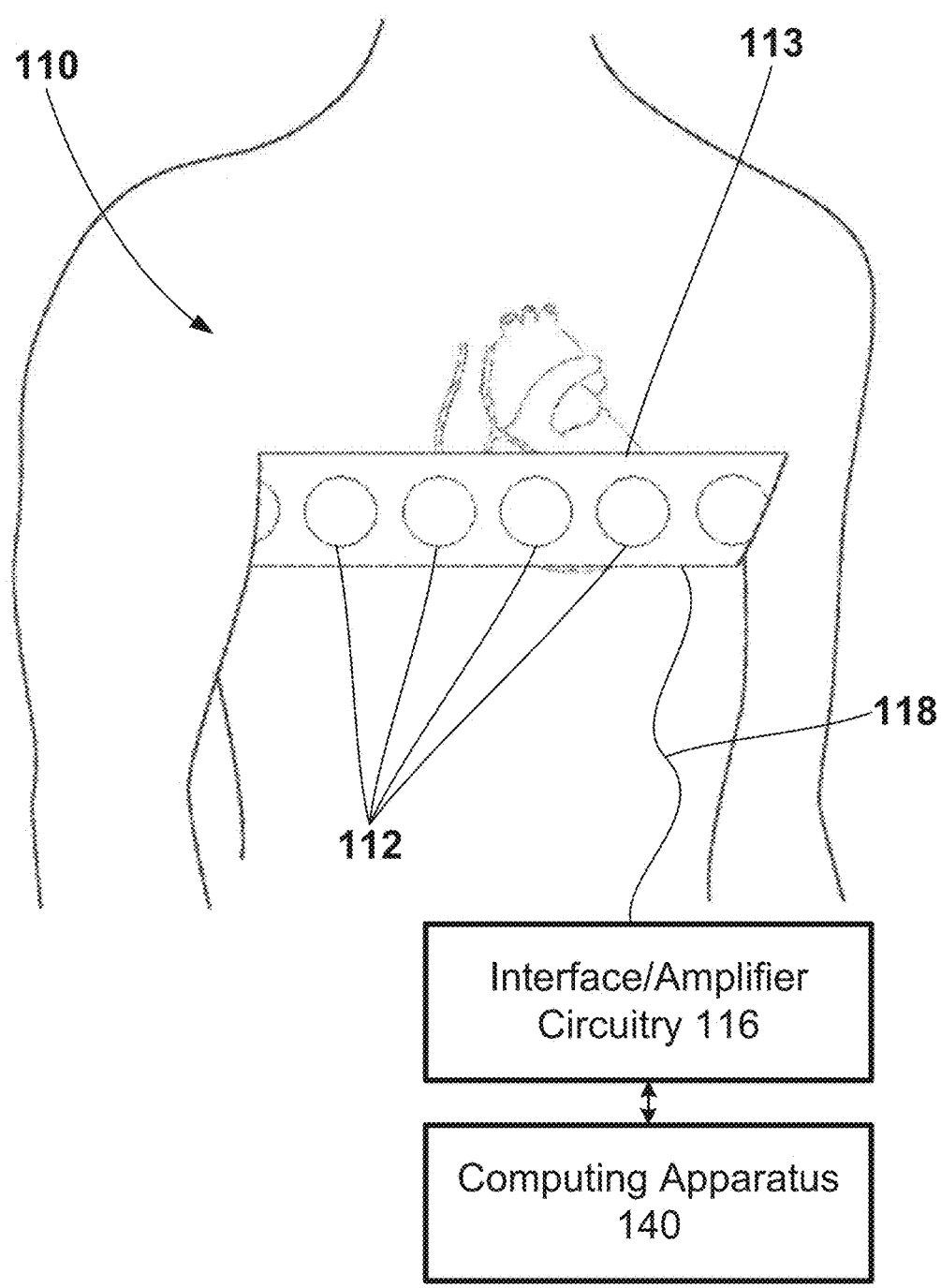
FIGS. 2-3 are diagrams of exemplary external electrode apparatus for measuring torso-surface potentials.

ECGs monitored by the electrode apparatus 110 of the patient's heart may be useful to evaluate cardiac therapy being delivered to a patient. In particular, one, or a single, QRS complex of a single cardiac cycle may be useful to evaluate the patient's cardiac health and/or any cardiac therapy being delivered to the patient. Such ECGs or ECG signals of a patient's heart may be monitored, or determined, using electrode apparatus 110 as shown in FIG. 1 and in FIGS. 2-3. The exemplary electrode apparatus 110 may be configured to measure body-surface potentials of a patient 14 and, more particularly, torso-surface potentials of a patient 14. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14. Still further, in other examples, the electrodes 112 may be part of, or located within, two sections of material or two "patches." One of the two sections or patches may be located on the anterior side of the torso of the patient 14 (to, e.g., monitor electrical signals representative of the anterior side of the patient's heart, measure surrogate cardiac electrical activation times representative of the anterior side of the patient's heart, etc.) and the other section or patch may be located on the posterior side of the torso of the patient 14 (to, e.g., monitor electrical signals representative of the posterior side of the patient's heart, measure surrogate cardiac electrical activation times representative of the posterior side of the patient's heart, etc.). And still further, in other examples, the electrodes 112 may be arranged in a top row and bottom row that extend from the anterior side of the patient 14 across the left side of the patient 14 to the anterior side of the patient 14. Yet still further, in other examples, the electrodes 112 may be arranged in a curve around the armpit area and may have an electrode-density that less dense on the right thorax that the other remaining areas.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of a patient. Other configurations may have more or fewer electrodes 112. It is to be understood that the electrodes 112 may not be arranged or distributed in an array extending all the way around or completely around the patient 14. Instead, the electrodes 112 may be arrange in an array that extends only part of the way or partially around the patient 14. For example, the electrode 112 may be distributed on the anterior, posterior, and left sides of the patient with less or no electrodes proximate the right side (including posterior and anterior regions of the right side).

The computing apparatus 140 may record and analyze the torso-surface potential signals sensed by electrodes 112 and amplified/conditioned by the interface/amplifier circuitry 116. The computing apparatus 140 may be configured to analyze the signals from the electrodes 112 to provide electrocardiogram (ECG) signals, information, or data from the patient's heart as will be further described herein.

Additionally, the computing apparatus 140 may be configured to provide graphical user interfaces depicting the ECGs including QRS complexes obtained using the electrode apparatus 110 as well as other information related thereto. Exemplary systems and methods may noninvasively use the electrical information collected using the electrode apparatus 110 to evaluate a patient's cardiac health and evaluate and configure cardiac therapy being delivered to the patient.

Further, the electrode apparatus 110 may further include reference electrodes and/or drive electrodes to be, e.g. positioned about the lower torso of the patient 14, that may be further used by the system 100. For example, the electrode apparatus 110 may include three reference electrodes, and the signals from the three reference electrodes may be combined to provide a reference signal. Further, the electrode apparatus 110 may use of three caudal reference electrodes (e.g., instead of standard references used in Wilson Central Terminal) to get a "true' unipolar signal with lesser noise from averaging three caudally located reference signals.

Figure 3:
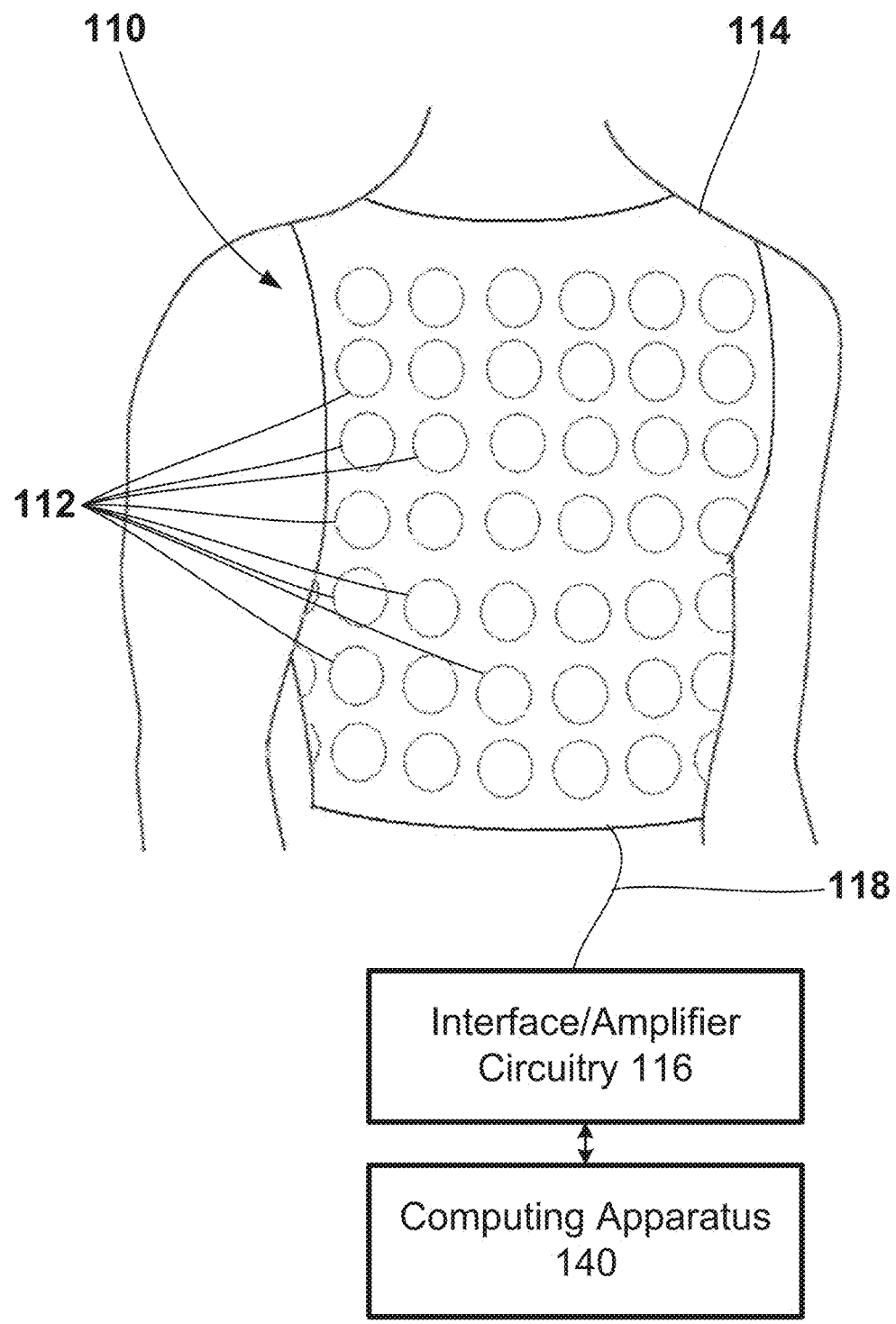

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 14, including, for example, the posterior, lateral, posterolateral, anterolateral, and anterior locations of the torso of a patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In some examples, there may be about 25 to about 256 electrodes 112 distributed around the torso of the patient 14, though other configurations may have more or fewer electrodes 112.

The exemplary systems and methods may be used to provide noninvasive assistance to a user in the evaluation of a patient's cardiac health and/or evaluation and configuration of cardiac therapy being presently-delivered to the patient (e.g., by an implantable medical device). For example, the exemplary systems and methods may be used to assist a user in the configuration and/or adjustment of one or more cardiac therapy settings for the cardiac therapy being delivered to a patient. Further, for example, the exemplary systems and methods may provide optimization of the A-V interval, or delay, of pacing therapy (e.g., left univentricular pacing therapy).

Figure 4:
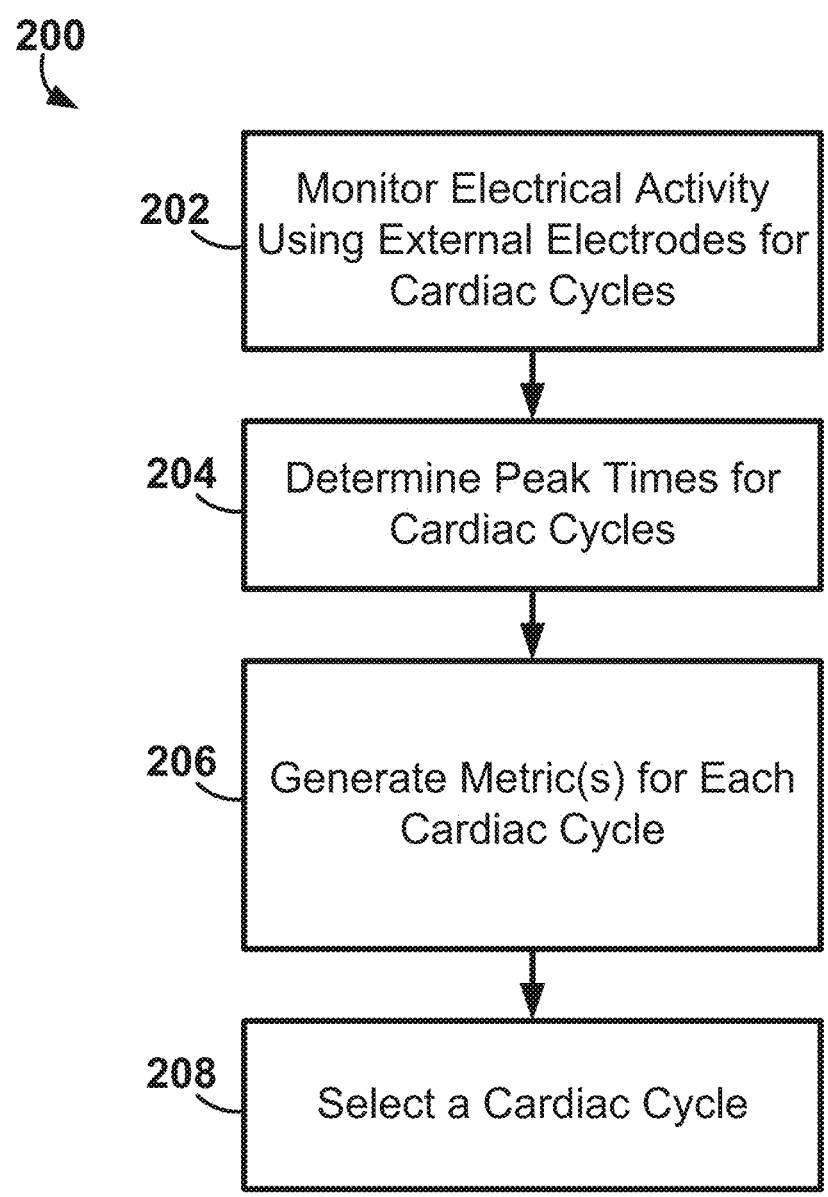
FIG. 4 is a block diagram of an exemplary method for selection of a cardiac cycle or heartbeat.

An exemplary method 200 of selecting a cardiac cycle, or heartbeat from a plurality of cardiac cycles, or heartbeats, is depicted in FIG. 4. More specifically, in this embodiment, the QRS complexes of electrical signals representative of the cardiac cycle may be selected since, e.g., the QRS complexes may be used to determine activation times and electrical heterogeneity information.

As shown, the method 200 includes monitoring electrical activity 202 of the patient using a plurality of external electrodes such as found on electrode apparatus 110 described herein. The electrical activity 202 may be monitored for a plurality of cardiac cycles or heartbeats. Further, the electrical activity 202 may be monitored for a selected period of time such as, e.g., five seconds. As described herein, some of the signals with respect to cardiac cycles, or more specifically, the QRS complexes related thereto may be irregular or have other undesirable characteristics or features that makes the signals corresponding to the cardiac cycles (e.g., QRS complexes) undesirable for further analysis with respect to a patient's cardiac health or cardiac therapy being delivered to the patient. It is to be understood that a more desirable signal representative of a cardiac cycle does not necessarily mean that the most "healthy" cardiac cycle is selected. Instead, a signal of a cardiac cycle having the desired signal characteristics for use in proper evaluation may be the cardiac cycle selected.

Thus, it may be described that the method 200 may analyze the electrical signals, or more specifically, the QRS complexes over a plurality of cardiac cycles to determine which cardiac cycle produced, or has, a desirable signal or QRS complex for further analysis. In other words, the method 200 may "filter out" undesirable signals during cardiac cycles, or heartbeats, from more desirable signals, and may, at least in one embodiment, determine the cardiac cycle, or heartbeat, and signal or QRS complex corresponding thereto that may be desirably used for further analysis.

Figure 5:
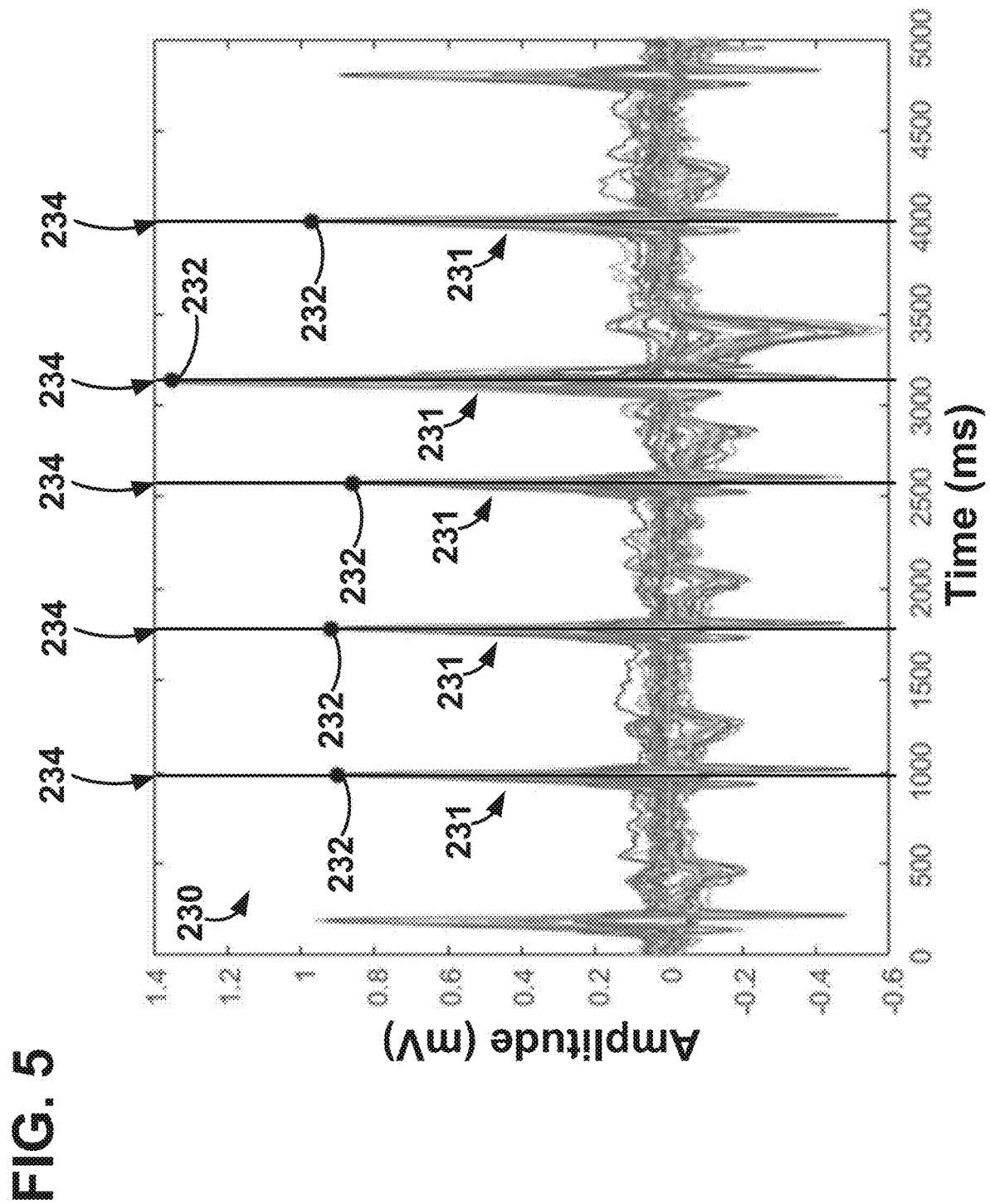
FIG. 5 is a graph of a plurality of electrical signals over a plurality of cardiac cycles including identified QRS peak locations.

The method 200 may determine, or identify, the peak times of the plurality of QRS complexes within the plurality of signals over the plurality of cardiac cycles 204. For example, a graph of a plurality of electrical signals 230 over time are depicted in FIG. 5. The plurality of electrical signals 230 include a plurality of cardiac cycles. In other words, the electrical signals 230 have been captured, or monitored, over a plurality of cardiac cycles. To identify the cardiac cycles, and more specifically, the QRS complexes 231 within the signals representative of the cardiac cycles, each of QRS peaks may be located within the plurality of signals 230. Five QRS peaks 232 are identified in FIG. 5 corresponding to five cardiac cycles. Further, the time at which each of the QRS peaks 232 occurs may be referred to as QRS peak time 234, each represented by a line.

Figure 6:
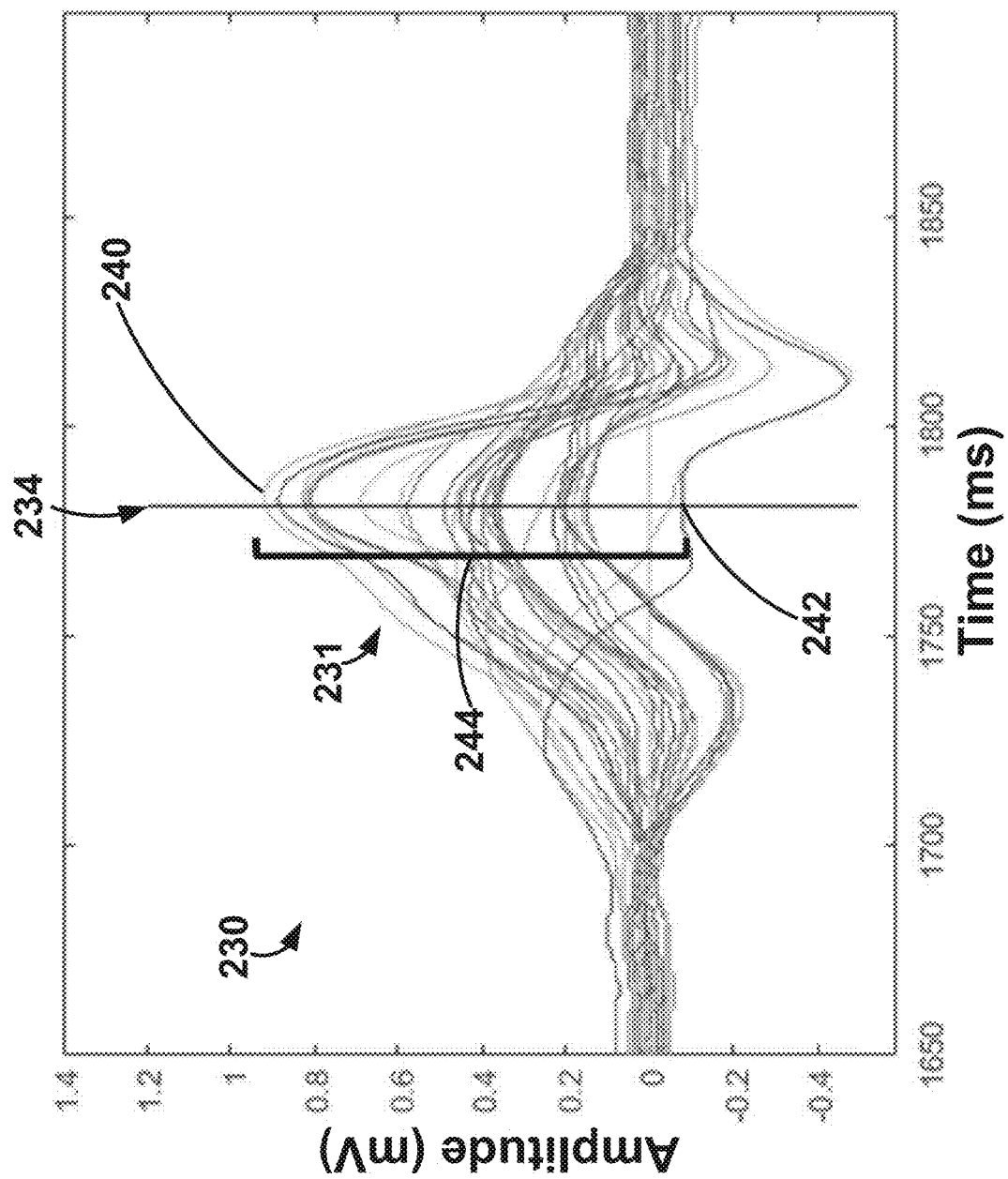
FIG. 6 is a graph of a plurality of electrical signals over a single cardiac cycle depicting various features of a QRS complex.

The peak times 234 may then be used to identify each of the QRS complexes 231. For example, a portion of each of the plurality of electrical signals 230 about each of the peak times 234 may be selected for further analysis. In other words, each of the plurality of electrical signals 230 may be "windowed" about their respective peak times 234 to provide segments of the plurality of electrical signals 230 that correspond to each cardiac cycle or QRS complex 231. For example, a graph of a plurality of electrical signals 230 over a single heartbeat or QRS complex 231 that has been window, or identified, from the peak time 234 at about 1780 milliseconds is depicted in FIG. 6.

Further, identifying the portion of each of the plurality of electrical signals 230 about each of the peak times 234, or more specifically, identifying the QRS complex may be executed by determining the onset and offset times of the QRS complex. Exemplary systems and methods of determining the onset and offset times of the QRS complex may be described in U.S. Prov. Pat. App. Ser. No. 62/471,938 filed on Mar. 15, 2017, and entitled "QRS OFFSET AND ONSET DETERMINATION," U.S. Pat. App. Pub. No. 2017/0143976 A1 filed on Dec. 2, 2016, and entitled "DETERMINING ONSETS AND OFFSETS OF CARDIAC DEPOLARIZATION AND REPOLARIZATION WAVES," U.S. Pat. App. Pub. No. 2016/0331258 A1 filed on Jul. 31, 2015, and entitled "DETERMINING ONSET OF CARDIAC DEPOLARIZATION AND REPOLARIZATION WAVES FOR SIGNAL PROCESSING," each of which is incorporated by reference in their entireties.

The method 200 may further include generating one or more (or a plurality) of metrics for each QRS complex 231 over the plurality cardiac cycles 206. In this example, five cardiac cycles (more specifically, in this example, five QRS complexes 231) are identified (see FIG. 5), and thus, one or more metrics may be generated, or calculated, for each of the five cardiac cycles. More specifically, in this example, one or more metrics may be generated, or calculated, for each of the five QRS complexes 231 corresponding to the five cardiac cycles.

One or more of the metrics generated 206 may be described as using at least two, or two or more, signals of the plurality of signals 230 monitored, or captured, by at least two, or two or more, electrodes. Further, one or more metrics generate 206 may use various submetrics. For example, one or more metrics generate 206 may use a single-cycle submetric that is based on at least two of the plurality of electrical signals during the cardiac cycle that is being presently analyzed. In other words, the single-cycle submetric may only use electrical signal data recorded during the window of the particular cardiac cycle for which the metric is being generated. Further, for example, one or more metrics generate 206 may use a cycle-series submetric that is based on at least two of the plurality of electrical signals during, or over, at least two cardiac cycles. In other words, the cycle-series submetric may use electrical signal data recorded during multiple windows of the cardiac cycles, including the cardiac cycle for which the metric is being generated.

Also, although the single-cycle submetric is described as using at least two of the plurality of electrical signals, it to be understood that the single-cycle submetric and/or the cycle-series submetric may use all of the electrical signals that are providing valid signals. Further, it to be understood that the single-cycle submetric and/or the cycle-series submetric may use a set of the electrical signals based on one or more pre-screening or filtering processes. Regardless, each of the submetrics may use two or more electrical signals. Additionally, each of the submetrics may be used to generate the one or more metrics generated 206, which will be further used by the process 208 as will be further described herein.

Exemplary single-cycle submetrics may include maximum amplitude, minimum amplitude, sum amplitude, R-R interval, peak-to-peak amplitude, dispersion (e.g., standard deviation, variance, range, etc.), polarity, window length, etc. The maximum amplitude 240 may be the value of the largest signal of at least two of the plurality of signals 230 (e.g., all of the plurality of signals) at peak time 234. The minimum amplitude 242 may be the value of the smallest signal at least two (e.g., all of the plurality of signals) of the plurality of signals 230 at peak time 234. The sum amplitude 244 may be the sum of at least two of all amplitude values of the plurality of signals 230 (e.g., all of the plurality of signals) at peak time 234. The R-R interval may be the time value from the peak time 234 to the peak time 234 of either the previous QRS complex or following QRS complex.

Exemplary cycle-series submetrics may be medians, modes, averages, quantiles, (maximum value−minimum value)/2, median after dropping outliers (e.g., at least one high value, at least one low value, etc.), average after dropping outliers (e.g., at least one high value, at least one low value, etc.), standard deviation, etc. of the single-cycle submetrics generated, or calculated, for each cardiac cycle or QRS complex. Further, it is to be understood that contact metrics could be used to eliminate signals from the calculations (such as medians), for example, if they have low peak-to-peak amplitudes or the like, to keep the calculations from getting artificially deflated. In other words, pre-processing step or processes may be used before computing any of the metrics or submetrics to eliminate outliers or undesired signal data.

Further, each metric generated for each cardiac cycle, or QRS complex, may be a fraction, or ratio, of the single-cycle submetric, which may be based on at least two of the plurality of electrical signals 230 during the present cardiac cycle being analyzed, the cycle-series submetric, which may be based on at least two of the plurality of electrical signals 230 during at least two cardiac cycles. In the example depicted in FIGS. 5-6, one metric could be generated based on a single-cycle submetric, which is based on all of the plurality of electrical signals 230 of the QRS complex having a peak time 234 of 1780 milliseconds (FIG. 6), and a cycle-series submetric, which is based on all of the plurality of signals 230 at each of the five peak times 234 (FIG. 5).

More specifically, a maximum amplitude metric, a minimum amplitude metric, a sum amplitude metric, and a R-R interval metric may be generated as follows:

$$\text{Maximum amplitude metric } (M_{max}) = \frac{\text{maximum signal value at peak time}}{\text{median(maximum signal values at all of the peak times)}} \quad (1)$$

$$\text{Minimum amplitude metric } (M_{min}) = \frac{\text{minimum signal value at peak time}}{\text{median(minimum signal values at all of the peak times)}} \quad (2)$$

$$\text{Sum amplitude metric } (M_{sum}) = \frac{\text{sum of all signal values at the peak time}}{\text{median(sum amplitudes at all of the peaks times)}} \quad (3)$$

$$\text{R-R interval metric } (M_{rr}) = \frac{\text{time interval between the current and previous peak times}}{\text{median(time intervals between peak times)}} \quad (4)$$

After at least one metric, or a plurality of metrics, have been generated for each cardiac cycle or heartbeat (QRS complex) 206, the method 200 may then select one or more of the cardiac cycles or heartbeats 208 based on at least the metrics. The selected one or more cardiac cycles or heartbeats 208 may then be used for further analysis of the patient's cardiac functionality and/or cardiac therapy being delivered to the patient. In one or more embodiments, a single cardiac cycles or heartbeat may be selected 208.

It is to be understood that selection one or more of the cardiac cycles or heartbeats 208 based on at least the generated metrics may be performed a plurality of different ways. One exemplary method, or process, 208 of selection one or more of the cardiac cycles, or heartbeats, 208 based on at least the generated metrics is depicted in FIGS. 7-10.

Figure 7:
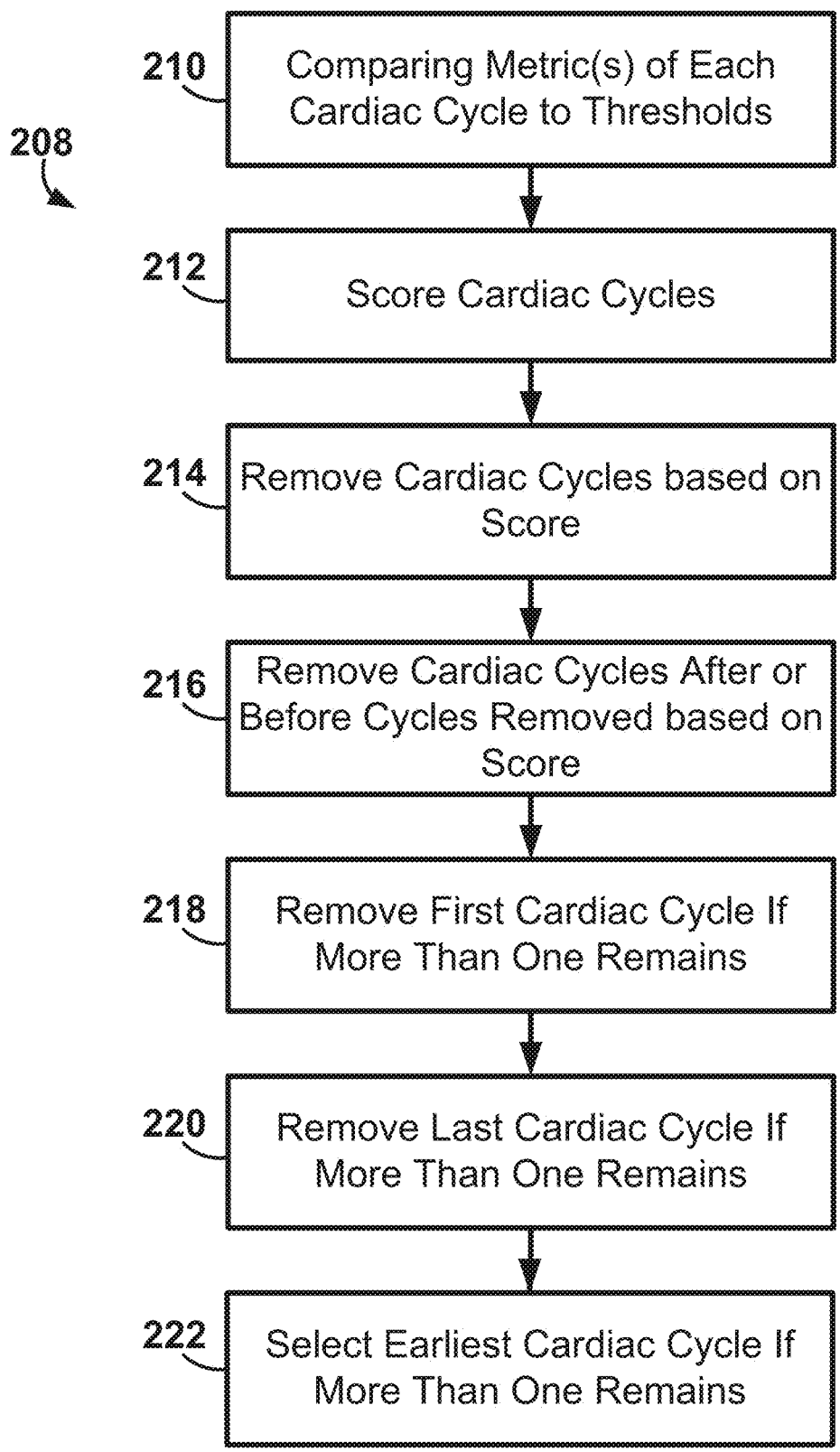
FIG. 7 is a block diagram of an exemplary selection process of the method of FIG. 4.

The method 208 of FIG. 7 may include comparing each metric of each cardiac cycle, or heartbeat, to a threshold 210, and then scoring each cardiac cycle, or heartbeat, 212 based on the comparison of each metric. For example, a table of exemplary metrics generated from the plurality of electrical signals 230 for five heartbeats is depicted in FIG. 8. Specifically, a maximum amplitude metric ($M_{max}$), a minimum amplitude metric ($M_{min}$), a sum amplitude metric ($M_{sum}$), and a R-R interval metric ($M_{rr}$) were generated for each of the five heartbeats as shown.

Each value of each metric for each heartbeat may then be compared to various thresholds to determine a score for each metric for each heartbeat. It is to be understood that a plurality of different thresholds may be used in a many different way as well as the scoring. One exemplary set of thresholds are depicted in the following Table 1:

TABLE 1

| Metric | Fails Threshold (score = 1) | Passes Threshold (score = 0) |
|---|---|---|
| Maximum metric ($M_{max}$) | $M_{max} < 0.75$ or $M_{max} > 1.25$ | $M_{max} > 0.75$ and $M_{max} < 1.25$ |
| Minimum metric ($M_{min}$) | $M_{min} < 0.75$ or $M_{min} > 1.25$ | $M_{min} > 0.75$ and $M_{min} < 1.25$ |

TABLE 1-continued

| Metric | Fails Threshold (score = 1) | Passes Threshold (score = 0) |
|---|---|---|
| Sum metric ($M_{sum}$) | $M_{sum} < 0.75$ or $M_{sum} > 1.25$ | $M_{sum} > 0.75$ and $M_{sum} < 1.25$ |
| R-R interval metric ($M_{rr}$) | $M_{rr} < 0.8$ | $M_{rr} > 0.8$ |

Each of the metrics depicted in FIG. 8 may be compared to the thresholds of Table 1 above, and assigned a score of 0 if the value of the metric passes the threshold and a score of 1 if the value of the metric fails the threshold as shown in the table of FIG. 9. Additionally shown, a score for each heartbeat may be tabulated by adding all the scores for the heartbeat as shown in the bottom row of the table of FIG. 9. In other words, each value in a column, each of which represents a heartbeat or cardiac cycle, may be added together to provide a score for that particular heartbeat or cardiac cycle. As shown, "Beat 1" has a score of "0," "Beat 2" has a score of "0," "Beat 3" has a score of "1," "Beat 4" has a score of "3," "Beat 5" has a score of "1." The exemplary method, or process, 208 of selecting a cardiac cycle, or heartbeat, may use, among other things, these scores, which, as described herein, are based on both of a single-cycle submetric and a cycle-series submetric to select one or more cardiac cycles, or heartbeats, for further analysis and evaluation.

It is to be understood that additional metrics may be further considered such as, for example, an electrode contact metric or a regional electrode contact metric. The electrode contact metric may be representative of an amount of the plurality of electrodes that captured a valid electrocardiographic signal from the tissue of the patient during the cardiac cycle. The regional electrode contact metric may be representative of an amount of the plurality of electrodes located proximate a selected region of the patient that captured a valid electrocardiographic signal from the tissue in the selection region of the patient during the cardiac cycle. In one or more embodiments, an electrode contact metric may be computed as a percentage of electrodes with valid electrocardiographic signals over each cardiac cycle and this metric may be used to select a cardiac cycle in addition to the other signal quality metrics described herein. For example, if all cardiac cycles over a period of time have the same score based on these metrics, the cardiac cycle with a maximum electrode contact metric may be used to resolve the tie and select a cardiac cycle for processing of activation times. An electrode contact metric may be computed for one or more regions of the torso such as e.g., the right thorax and/or the left thorax. In another embodiment, cardiac cycles with a electrode contact metric less than a threshold may not be eligible for selection. Exemplary values of such threshold may be 70%, 65%, 60%, etc. Exemplary systems and methods for use in providing electrode contact metrics and identifying electrodes provide valid sensing signals may be described in U.S. patent application Ser. No. 14/227,955 filed on Mar. 27, 2014 and entitled "Systems, Methods, and Interfaces for Identifying Effective Electrodes," which is incorporated herein by reference in its entirety.

Additionally, the scoring as described with respect to Table 1 could be "weighted." For example, in one embodiment the R-R interval metric could have a fail score of 2.

Further, some of the metrics could be analyzed first, beats removed, and then the remainder of the metrics may be analyzed for the remaining beats. For example, the R-R interval metric may be analyzed, and if any beat is removed, the beat following removed beat may be removed as well as the prior beat, potentially. Then, the remainder of the metrics may be used to choose the beat. Further, for example, in another embodiment, the R-R interval metric may be worth 1.5 and sum metric may be worth 0.5.

The exemplary method 208 may include removing from consideration of selection cardiac cycles, or heartbeats, based on the score 214. For example, the score may be compared to a scoring threshold value, and depending on whether the score is greater than, equal to, or less than the scoring threshold value may determine whether the cardiac cycle is kept or removed from consideration. For instance, any cardiac cycle, or heartbeat, having or defining a score greater than a scoring threshold value may be removed from further consideration and, conversely, any cardiac cycle, or heartbeat, having or defining a score less than or equal to the scoring threshold value may be remaining. In this embodiment, the scoring threshold value may be "2." As such, any heartbeats having a score greater than 2 may be disregarded, and not further considered for selection.

If there is only a single heartbeat or cardiac cycle remaining, the method 208 may end, and the final remaining heartbeat or cardiac cycle may be selected for further evaluation.

The exemplary method 208 may further include removing from consideration of selection heartbeats that follow heartbeats having a score greater than the scoring threshold value. In other words, the heartbeat occurring immediately after a heartbeat that fails to be less than the threshold value may also be removed from further consideration of selection. For example, if a particular heartbeat such as "Beat 17" is removed for having a score greater than the scoring threshold, then the following "Beat 18" may also be removed from consideration. Likewise, if still more than one cardiac cycle remains, the beat preceding a heartbeat that with a failed threshold may be removed from consideration. For example, if a particular heartbeat such as "Beat 17" is removed for having a score greater than the scoring threshold, then the preceding "Beat 16" may also be removed from consideration.

If still more than one cardiac cycle remains, the first cardiac cycle in the plurality of cardiac cycle from the plurality of signals may be removed from consideration 218. Likewise, if still more than one cardiac cycle remains, the last cardiac cycle in the plurality of cardiac cycles from the plurality of signals may be removed from consideration 220. Lastly, if more than one cardiac cycle remains out of the plurality of cardiac cycles, the earliest cardiac cycle still remaining may be selected for further evaluation and analysis 222.

Figure 10:
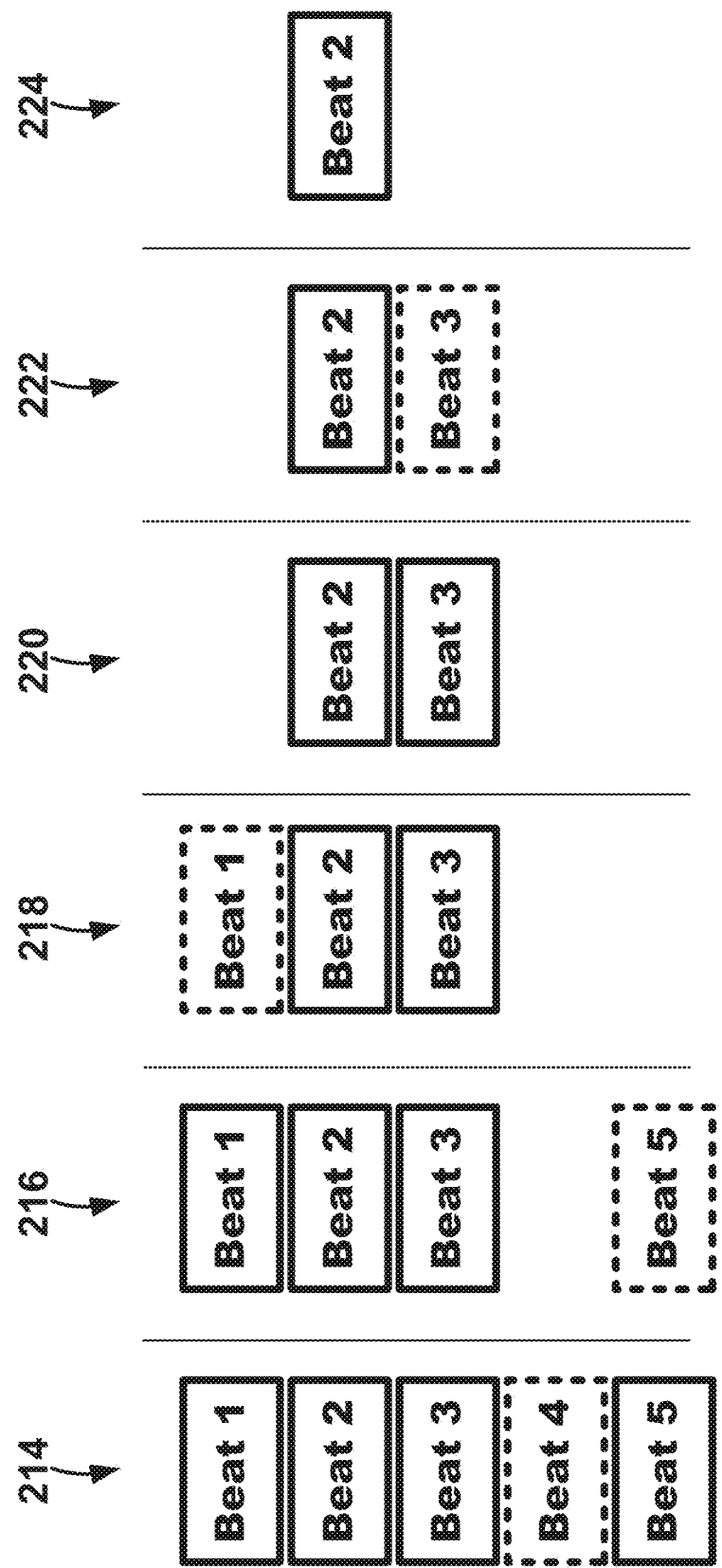
FIG. 10 depicts an exemplary selection process of a cardiac cycle from the five cardiac cycles of FIGS. 8-9.

An exemplary selection process of a heartbeat, or cardiac cycle, from the five heartbeats of FIGS. 8-9 is depicted in FIG. 10. As shown, the five heartbeats, or cardiac cycles, are represented by boxes and are evaluated chronologically from left to right using the method 208. When a heartbeat is to be removed based on a particular step or process of the method 208, the box representing the heartbeat is represented by dashed lines, and is then removed from the figure for the next step or process.

First, the heartbeats with a score greater than 2, i.e., the scoring threshold value, may be removed 214. As shown in FIG. 9, "Beat 4" has a score of 3, which is greater than 2, and thus "Beat 4" may be removed. Next, since more than one heartbeat remains, any beat following a beat with a score greater than 2, i.e., the scoring threshold value, may be removed 216. Four beats remain, and thus "Beat 5," which follows "Beat 4," may be removed.

Further, since more than one heartbeat remains, the first beat of the plurality beats may be removed 218, and thus, "Beat 1" is removed. Still further, although more than one heartbeat remains, the last beat of the plurality beats has already been removed, and thus, no beat is removed in process 220. Lastly, if more than one heartbeat remains, the earliest remaining heartbeat may be selected for further evaluation and analysis 222. Since "Beat 2" and "Beat 3" remains, "Beat 3" is removed leaving "Beat 2" to be selected 224 since "Beat 2" occurs earlier than "Beat 3."

In other words, the exemplary systems and methods may be described as using QRS complex quality ranking. For instance, several metrics are used to compare electrical characteristics at a single pre-defined time point for each beat within the 5-second period against that of the median value for all beats across multiple body surface electrodes. Such metrics include: maximum and minimum signal values, sum of all signal values, and peak-to-peak interval. The metrics for each beat are compared to a threshold and are passed or failed for each characteristic. Other metrics may include percentage of electrodes that are in good contact and measure valid ECG signals for each QRS complex as contact for a given electrode and consequently the quality of signal may be variable over the 5-second period. Metrics of quality of signal or contact may be measured based on skin-electrode impedance and amplitude.

Further, a score using the pass or fail assessments may then be used to determine which beats are irregular from the median beat value and are likely not representative of the electrical conduction for the current pacing parameters. These irregular beats are removed from the candidate pool. Additional candidate beats are removed for following irregular beats and for being at the beginning or end of the signal collection.

Still further, the exemplary systems and methods may collect five seconds of data for each pacing configuration. However, it may be computationally expensive and redundant to process all beats in each 5-second clip for CRT optimization. Thus, the exemplary systems and methods may be described as quantifying and scoring the quality of each beat against all others in the time series, and then determine which QRS complex to process additionally. The quality check may identify irregular beats, such as PVCs, and the selection process selects the beat that is most representative of the median.

As described herein, the exemplary systems and methods described herein may be used with respect to the implantation and configuration of an implantable medical device (IMD) and/or one or more leads configured to be located proximate one or more portions of a patient's heart. For example, the exemplary systems and methods may be used in conjunction with an exemplary therapy system 10 described herein with reference to FIGS. 11-13.

Figure 11:
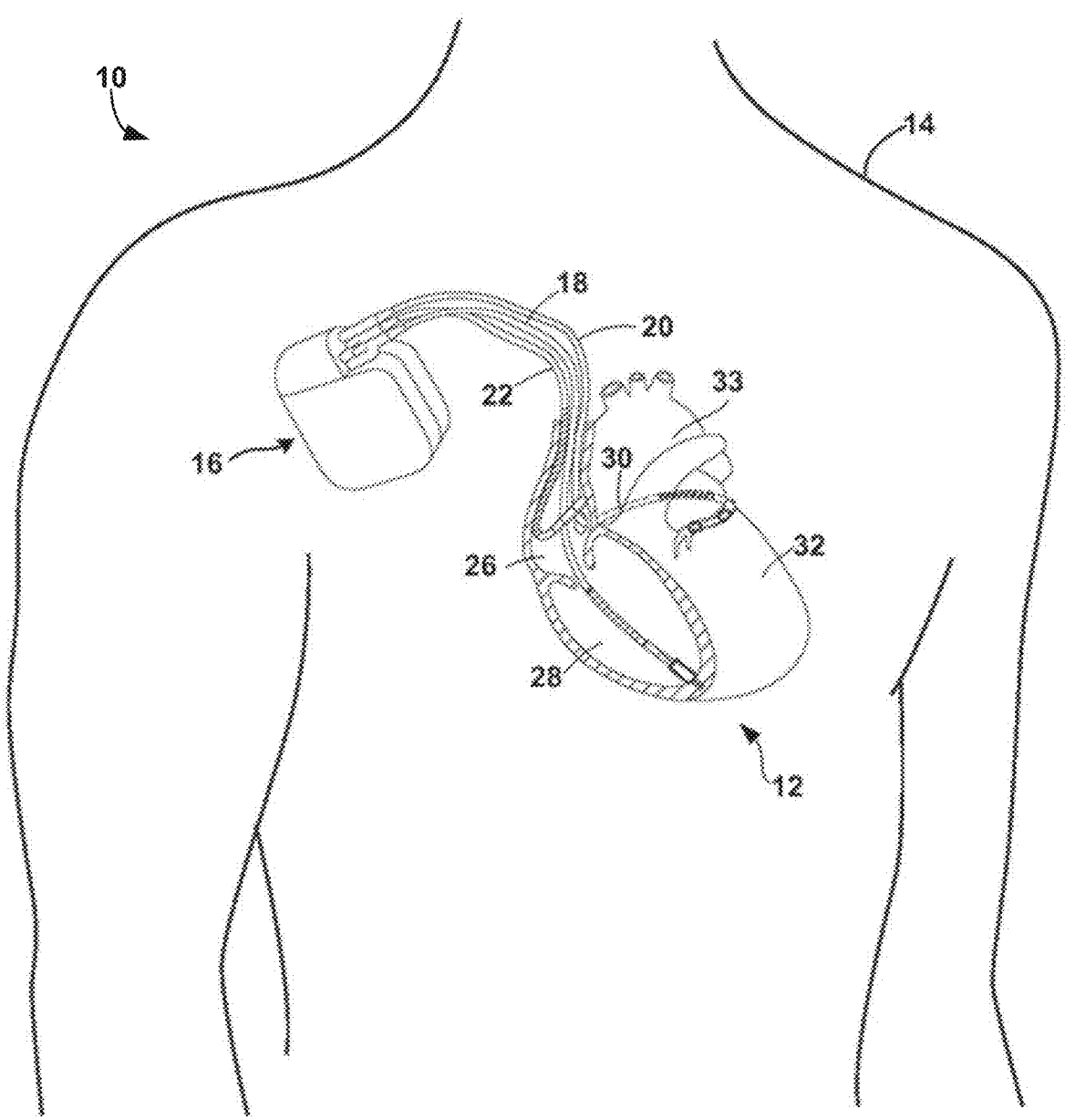
FIG. 11 is a diagram of an exemplary system including an exemplary implantable medical device (IMD).

FIG. 11 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals to and/or measures, or monitors electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 11, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12. Although the system 10 includes a RV lead 18, it is to be understood the exemplary systems and methods described herein may not utilize the electrodes located on the RV lead 18 for sensing and/or pacing. Further, it is to be understood that the system 10 is merely one example, and that the exemplary systems and methods described herein may utilize systems that do not include a RV lead 18 (e.g., for sensing and/or pacing).

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., A-V delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 12A:
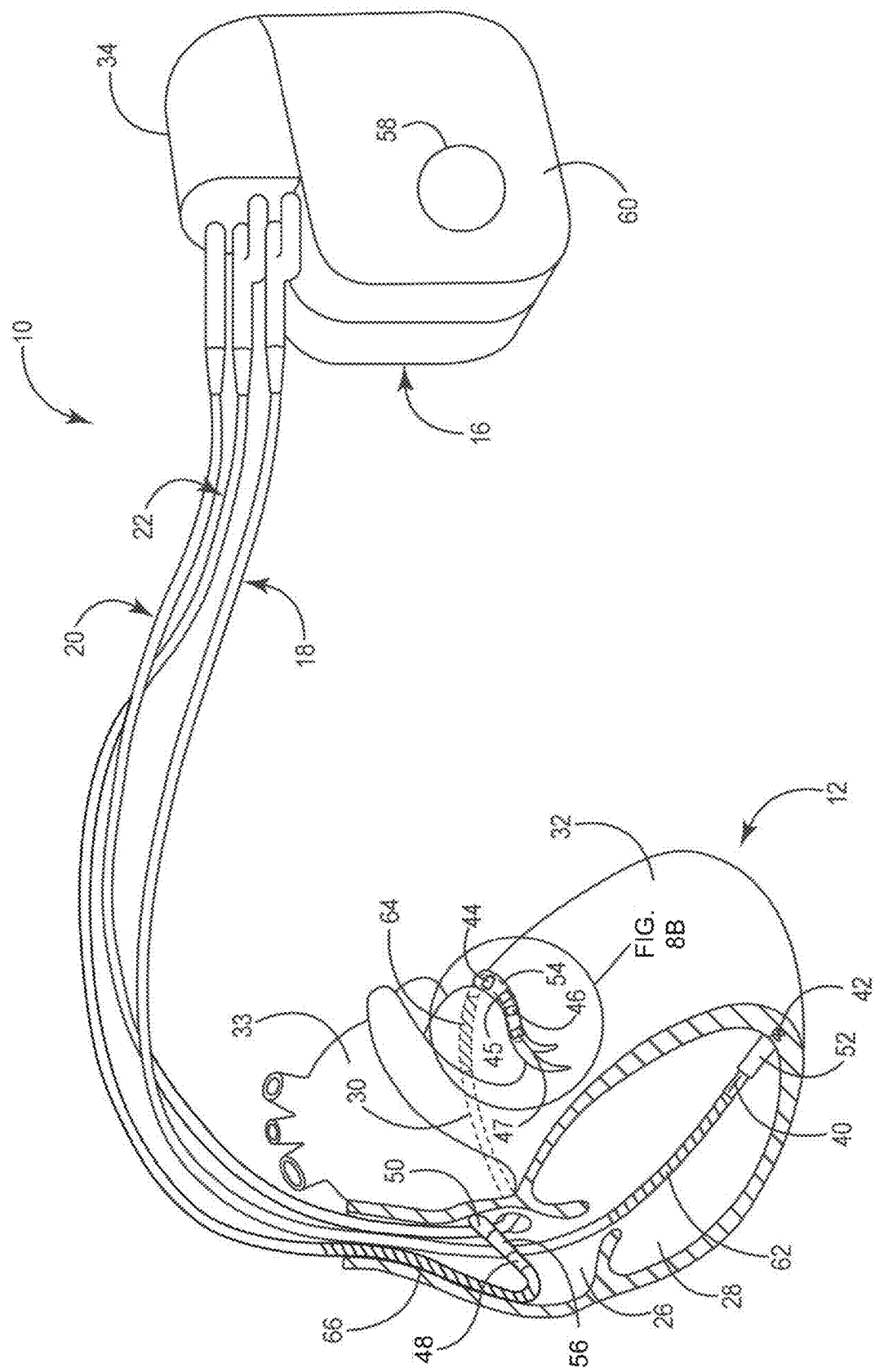
FIG. 12A is a diagram of the exemplary IMD of FIG. 11.
Figure 12B:
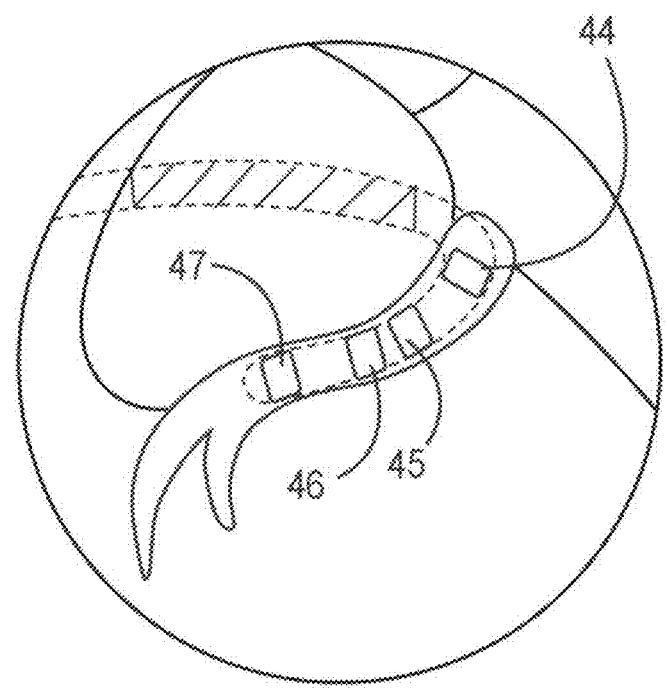
FIG. 12B is a diagram of an enlarged view of a distal end of the electrical lead disposed in the left ventricle of FIG. 12A.

FIGS. 12A-12B are conceptual diagrams illustrating the IMD 16 and the leads 18, 20, 22 of therapy system 10 of FIG. 11 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 $mm^2$ to about 5.8 $mm^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g., about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The sensed electrical signals may be used to adjust one or more pacing parameters such as, e.g., A-V interval, V-V interval, etc. to provide optimal and/or effective cardiac functionality. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 12A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. In other words, any of electrodes 40, 42, 44, 45, 46, 47, 48, 50, 58 may be used in combination to form a sensing vector, e.g., a sensing vector that may be used to evaluate and/or analyze the effectiveness of pacing therapy. It is to be understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 12A, the housing 60 may enclose a therapy delivery module that may include a stimulation generator for generating cardiac pacing pulses and defibrillation or cardioversion shocks, as well as a sensing module for monitoring electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining electrode effectiveness, for use in analyzing pacing therapy effectiveness, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy systems 10 illustrated in FIGS. 11-13 are merely a couple of examples. In other examples, the therapy system may include epicardial leads and/or patch electrodes instead of or in addition to the transvenous leads 18, 20, 22 illustrated in FIG. 11. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 11). An exemplary leadless system may be described in U.S. patent application Ser. No. 14/173,288 filed on Feb. 5, 2014 and entitled "Systems and Methods for Leadless Cardiac Resynchronization Therapy," which is incorporated herein by reference in its entirety. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include less than or more than three transvenous leads. In at least one embodiment, the therapy system that provides pacing, or electrical stimulation, therapy to the heart 12 may only provide left univentricular pacing therapy with using, or including, sensing or pacing electrodes located in the left ventricle. In these left univentricular pacing systems, at least one pacing and/or sensing electrode may be located in the patient's left ventricle and at least one pacing and/or sensing electrode may be located in one or both the right atrium and left atrium. Still further, other therapy systems may include a single lead that extends from the IMD 16 into the right atrium 26 or the right ventricle 28, or two leads that extend into a respective one of the right atrium 26 and the right ventricle 28.

Figure 13A:
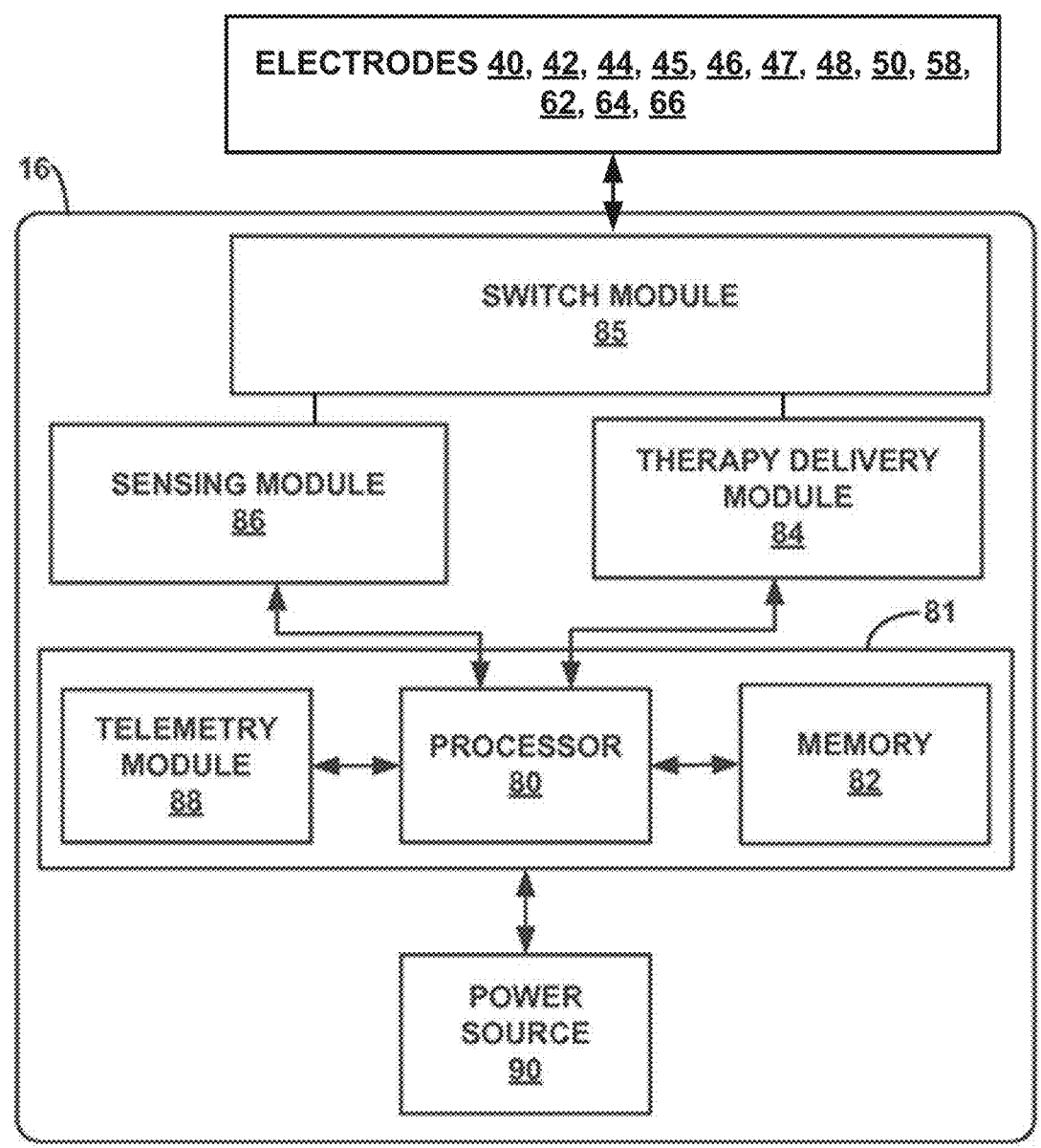
FIG. 13A is a block diagram of an exemplary IMD, e.g., the systems of FIGS. 11-12.

FIG. 13A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., A-V delays, V-V delays, pacing pulses with the amplitudes, pulse widths, frequency, or electrode polarities, etc., which may be specified by one or more selected therapy programs (e.g., A-V and/or V-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy using a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activation times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals (e.g., intrinsic A-V conduction times), which may be analyzed by, e.g., the processor 80 in response to the occurrence of a pace or sense interrupt to determine whether the patient's heart 12 is presently exhibiting atrial or ventricular tachyarrhythmia.

The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 13B:
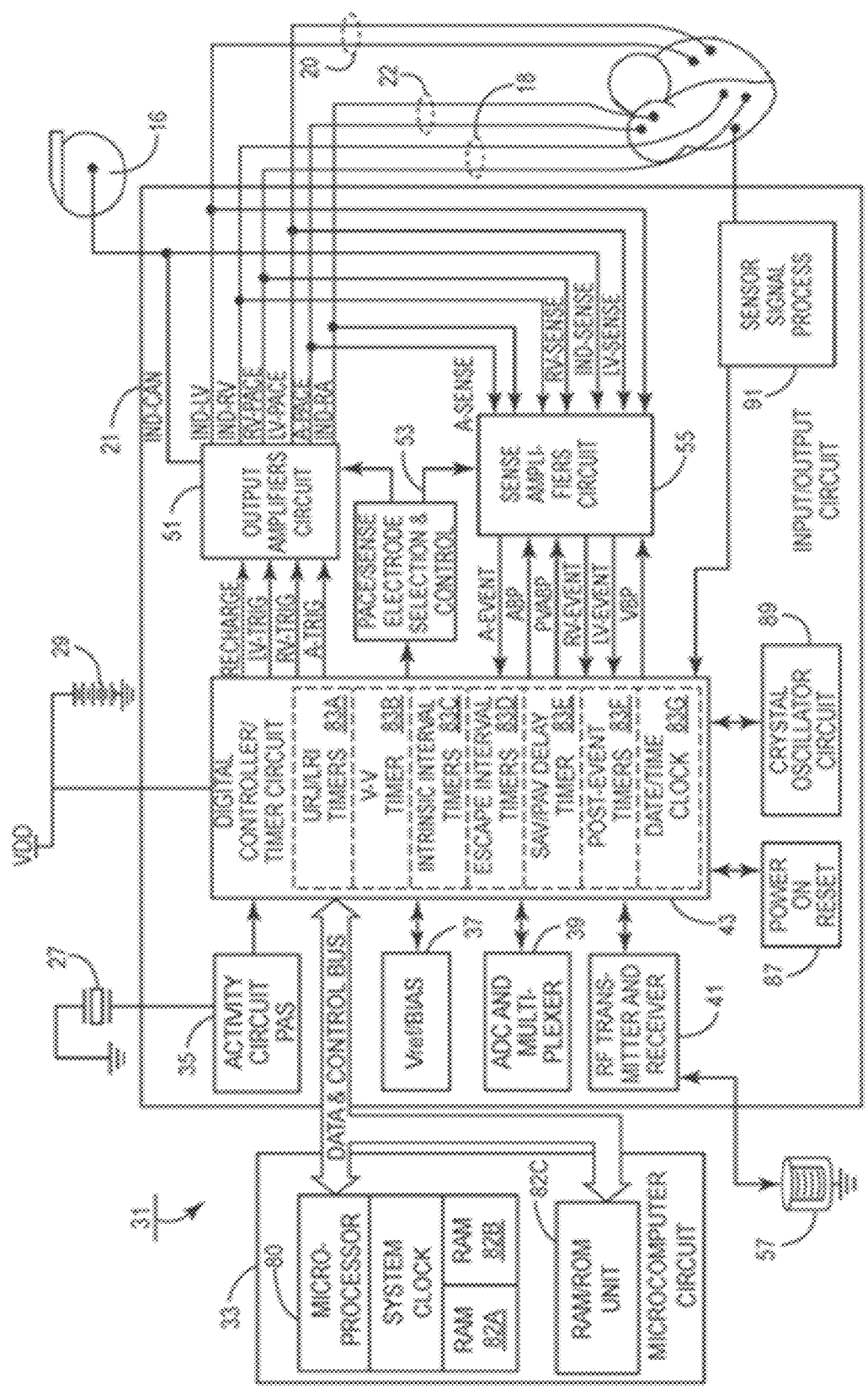
FIG. 13B is another block diagram of an exemplary IMD (e.g., an implantable pulse generator) circuitry and associated leads employed in the systems of FIGS. 11-12.

FIG. 13B is another embodiment of a functional block diagram for IMD 16. FIG. 13B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. An output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative A-V delay intervals and/or V-V intervals, and the energy delivered to the ventricles and/or atria.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 321 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp delay) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG.

The microprocessor 80 also optionally calculates A-V delays, V-V delays, post-ventricular time periods, and post-atrial time periods that vary with the sensor based escape interval established in response to the RCP(s), intrinsic A-V conductions times, intrinsic heart rate, and/or any other parameter or metric.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV, and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

ILLUSTRATIVE EMBODIMENTS

Embodiment 1. A system for use in cardiac evaluation comprising:

electrode apparatus comprising a plurality of external electrodes to be located proximate tissue of a patient; and computing apparatus comprising one or more processors, the computing apparatus coupled to the electrode apparatus and configured to:

monitoring electrical activity using the plurality of electrodes to provide a plurality of electrical signals over a plurality of cardiac cycles, generate at least one metric for each cardiac cycle based on a single-cycle submetric and a cycle-series submetric, wherein the single-cycle submetric is based on at least two of the plurality of electrical signals during the cardiac cycle and the cycle-series submetric is based on at least two of the plurality of electrical signals during at least two cardiac cycles, and select a cardiac cycle of the plurality of cardiac cycles based on the at least one metric.

Embodiment 2. The system of embodiment 1, wherein the single-cycle submetric is a value generated from at least two of the plurality of electrical signals at a peak time during the cardiac cycle and the cycle-series submetric is a value generated from at least two electrical signals of the plurality of electrical signals at peak times during the at least two cardiac cycles.

Embodiment 3. The system as in any one of embodiments 1-3, wherein the at least one metric for each cardiac cycle comprises a maximum amplitude metric, wherein the single-cycle submetric is a maximum value across at least two of the plurality electrical signals at a peak time during cardiac cycle, wherein the cycle-series submetric is a composite maximum value based on all of the maximum values of at least two of the plurality of electrical signals at peak times during the at least two cardiac cycles, wherein the maximum amplitude metric is the single-cycle submetric divided by the cycle-series submetric.

Embodiment 4. The system of embodiment 3, wherein the composite maximum value is the median of the maximum values of the at least two of the plurality of electrical signals at the peak times during the at least two cardiac cycles.

Embodiment 5. The system as in any one of embodiments 1-4, wherein the at least one metric for each cardiac cycle comprises a minimum amplitude metric, wherein the single-cycle submetric is a minimum value across at least two of the plurality electrical signals at a peak time during cardiac cycle, wherein the cycle-series submetric is a composite minimum value based on all of the minimum values of at least two of the plurality of electrical signals at peak times during the at least two cardiac cycles, wherein the minimum amplitude metric is the single-cycle submetric divided by the cycle-series submetric.

Embodiment 6. The system as in any one of embodiments 1-5, wherein the at least one metric for each cardiac cycle comprises a sum amplitude metric, wherein the single-cycle submetric is a sum of at least two of the plurality of electrical signals at a peak time during the cardiac cycle, wherein the cycle-series submetric is a composite sum value based on at least two of the plurality of electrical signals at peak times during the at least two cardiac cycles, wherein the sum amplitude metric is the single-cycle submetric divided by the cycle-series submetric.

Embodiment 7. The system as in any one of embodiments 1-6, wherein the at least one metric for each cardiac cycle comprises an interval metric, wherein the single-cycle submetric is a time interval between a peak time of the cardiac cycle and a peak time of a previous or following cardiac cycle of the plurality of cardiac cycles, wherein the cycle-series submetric is a composite interval value based on all time intervals between peak times of at least two cardiac cycles.

Embodiment 8. The system as in any one of embodiments 1-7, wherein the at least one metric for each cardiac cycle comprises an electrode contact metric, wherein the electrode contact metric is representative of an amount of the plurality of electrodes that captured a valid electrocardiographic signal from the tissue of the patient during the cardiac cycle.

Embodiment 9. The system as in any one of embodiments 1-8, wherein the at least one metric for each cardiac cycle comprises a regional electrode contact metric, wherein the regional electrode contact metric is representative of an amount of the plurality of electrodes located proximate a selected region of the patient that captured a valid electrocardiographic signal from the tissue in the selection region of the patient during the cardiac cycle.

Embodiment 10. The system as in any one of embodiments 1-9, wherein selecting a cardiac cycle of the plurality of cardiac cycles based on the at least one metric comprises:

comparing the at least one metric for each cardiac cycle to at least one threshold value to assign a score the cardiac cycle.

Embodiment 11. The system as in any one of embodiments 1-10, wherein selecting a cardiac cycle of the plurality of cardiac cycles based on the at least one metric comprises:

assigning a score to each cardiac cycle of the plurality of cardiac cycles; and selecting the cardiac cycle of the plurality of cardiac cycles having the best score.

Embodiment 12. The system as in any one of embodiments 1-11, wherein selecting a cardiac cycle of the plurality of cardiac cycles based on the at least one metric comprises:

assigning a score to each cardiac cycle of the plurality of cardiac cycles; and removing from consideration of selection cardiac cycles of the plurality of cardiac cycles having a score greater than a scoring threshold value.

Embodiment 13. The system of embodiment 12, wherein selecting a cardiac cycle of the plurality of cardiac cycles based on the at least one metric comprises removing from consideration of selection cardiac cycles of the plurality of cardiac cycles following or preceding cardiac cycles having a score greater than the scoring threshold value.

Embodiment 14. The system as in any one of embodiments 1-13, wherein selecting a cardiac cycle of the plurality of cardiac cycles based on the at least one metric comprises removing from consideration of selection the cardiac cycle that occurs last if at least two cardiac cycles remain being considered for selection.

Embodiment 15. The system as in any one of embodiments 1-14, wherein the computing apparatus is further configured to execute generating electrical activation times based on the plurality of cardiac signals of the selected cardiac cycle.

Embodiment 16. A method for use in cardiac evaluation comprising:

monitoring electrical activity from tissue of a patient using a plurality of electrodes to generate a plurality of electrical signals over a plurality of cardiac cycles;

generating at least one metric for each cardiac cycle based on a single-cycle submetric and a cycle-series submetric, wherein the single-cycle submetric is based on at least two of the plurality of electrical signals during the cardiac cycle and the cycle-series submetric is based on at least two of the plurality of electrical signals during at least two cardiac cycles; and selecting a cardiac cycle of the plurality of cardiac cycles based on the at least one metric.

Embodiment 17. The method of embodiment 16, wherein the single-cycle submetric is a value generated from at least two of the plurality of electrical signals at a peak time during the cardiac cycle and the cycle-series submetric is a value generated from at least two electrical signals of the plurality of electrical signals at peak times during the at least two cardiac cycles.

Embodiment 18. The method as in any one of embodiments 16-17, wherein the at least one metric for each cardiac cycle comprises a maximum amplitude metric, wherein the single-cycle submetric is a maximum value across at least two of the plurality electrical signals at a peak time during cardiac cycle, wherein the cycle-series submetric is a composite maximum value based on all of the maximum values of at least two of the plurality of electrical signals at peak times during the at least two cardiac cycles, wherein the maximum amplitude metric is the single-cycle submetric divided by the cycle-series submetric.

Embodiment 19. The method of embodiment 18, wherein the composite maximum value is the median of the maximum values of the at least two of the plurality of electrical signals at the peak times during the at least two cardiac cycles.

Embodiment 20. The method as in any one of embodiments 16-19, wherein the at least one metric for each cardiac cycle comprises a minimum amplitude metric, wherein the single-cycle submetric is a minimum value across at least two of the plurality electrical signals at a peak time during cardiac cycle, wherein the cycle-series submetric is a composite minimum value based on all of the minimum values of at least two of the plurality of electrical signals at peak times during the at least two cardiac cycles, wherein the minimum amplitude metric is the single-cycle submetric divided by the cycle-series submetric.

Embodiment 21. The method as in any one of embodiments 16-20, wherein the at least one metric for each cardiac cycle comprises a sum amplitude metric, wherein the single-cycle submetric is a sum of at least two of the plurality of electrical signals at a peak time during the cardiac cycle, wherein the cycle-series submetric is a composite sum value based on at least two of the plurality of electrical signals at peak times during the at least two cardiac cycles, wherein the sum amplitude metric is the single-cycle submetric divided by the cycle-series submetric.

Embodiment 22. The method as in any one of embodiments 16-21, wherein the at least one metric for each cardiac cycle comprises an interval metric, wherein the single-cycle submetric is a time interval between a peak time of the cardiac cycle and a peak time of a previous or following cardiac cycle of the plurality of cardiac cycles, wherein the cycle-series submetric is a composite interval value based on all time intervals between peak times of at least two cardiac cycles.

Embodiment 23. The method as in any one of embodiments 16-22, wherein the at least one metric for each cardiac cycle comprises an electrode contact metric, wherein the electrode contact metric is representative of an amount of the plurality of electrodes that captured a valid electrocardiographic signal from the tissue of the patient during the cardiac cycle.

Embodiment 24. The method as in any one of embodiments 16-23, wherein the at least one metric for each cardiac cycle comprises a regional electrode contact metric, wherein the regional electrode contact metric is representative of an amount of the plurality of electrodes located proximate a selected region of the patient that captured a valid electrocardiographic signal from the tissue in the selection region of the patient during the cardiac cycle.

Embodiment 25. The method as in any one of embodiments 16-24, wherein selecting a cardiac cycle of the plurality of cardiac cycles based on the at least one metric comprises: comparing the at least one metric for each cardiac cycle to at least one threshold value to assign a score the cardiac cycle.

Embodiment 26. The method as in any one of embodiments 16-25, wherein selecting a cardiac cycle of the plurality of cardiac cycles based on the at least one metric comprises: assigning a score to each cardiac cycle of the plurality of cardiac cycles; and selecting the cardiac cycle of the plurality of cardiac cycles having the best score.

Embodiment 27. The method as in any one of embodiments 16-26, wherein selecting a cardiac cycle of the plurality of cardiac cycles based on the at least one metric comprises: assigning a score to each cardiac cycle of the plurality of cardiac cycles; and removing from consideration of selection cardiac cycles of the plurality of cardiac cycles having a score greater than a scoring threshold value.

Embodiment 28. The method of embodiment 27, wherein selecting a cardiac cycle of the plurality of cardiac cycles based on the at least one metric comprises removing from consideration of selection cardiac cycles of the plurality of cardiac cycles following or preceding cardiac cycles having a score greater than the scoring threshold value.

Embodiment 29. The method as in any one of embodiments 16-28, wherein selecting a cardiac cycle of the plurality of cardiac cycles based on the at least one metric comprises removing from consideration of selection the cardiac cycle that occurs last if at least two cardiac cycles remain being considered for selection.

Embodiment 30. The method as in any one of embodiments 16-29, wherein the method further comprises generating electrical activation times based on the plurality of cardiac signals of the selected cardiac cycle.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in cardiac evaluation comprising:
electrode apparatus comprising a plurality of external electrodes to be located proximate tissue of a patient; and
computing apparatus comprising one or more processors, the computing apparatus coupled to the electrode apparatus and configured to:
monitoring electrical activity using the plurality of electrodes to provide a plurality of electrical signals over a plurality of cardiac cycles,
generate at least one metric for each cardiac cycle based on a single-cycle submetric and a cycle-series submetric, wherein the single-cycle submetric is based on at least two of the plurality of electrical signals during the cardiac cycle and the cycle-series submetric is based on at least two of the plurality of electrical signals during at least two cardiac cycles, wherein the at least one metric for each cardiac cycle comprises an electrode contact metric, wherein the electrode contact metric is representative of an amount of the plurality of electrodes that captured a valid electrocardiographic signal from the tissue of the patient during the cardiac cycle, and
select a cardiac cycle of the plurality of cardiac cycles based on the at least one metric.

2. The system of claim 1, wherein the single-cycle submetric is a value generated from at least two of the plurality of electrical signals at a peak time during the cardiac cycle and the cycle-series submetric is a value generated from at least two electrical signals of the plurality of electrical signals at peak times during the at least two cardiac cycles.

3. The system of claim 1, wherein the at least one metric for each cardiac cycle comprises a maximum amplitude metric, wherein the single-cycle submetric is a maximum value across at least two of the plurality electrical signals at a peak time during cardiac cycle, wherein the cycle-series submetric is a composite maximum value based on all of the maximum values of at least two of the plurality of electrical signals at peak times during the at least two cardiac cycles, wherein the maximum amplitude metric is the single-cycle submetric divided by the cycle-series submetric.

4. The system of claim 3, wherein the composite maximum value is the median of the maximum values of the at least two of the plurality of electrical signals at the peak times during the at least two cardiac cycles.

5. The system of claim 1, wherein the at least one metric for each cardiac cycle comprises a minimum amplitude metric, wherein the single-cycle submetric is a minimum value across at least two of the plurality electrical signals at a peak time during cardiac cycle, wherein the cycle-series submetric is a composite minimum value based on all of the minimum values of at least two of the plurality of electrical signals at peak times during the at least two cardiac cycles, wherein the minimum amplitude metric is the single-cycle submetric divided by the cycle-series submetric.

6. The system of claim 1, wherein the at least one metric for each cardiac cycle comprises a sum amplitude metric, wherein the single-cycle submetric is a sum of at least two of the plurality of electrical signals at a peak time during the cardiac cycle, wherein the cycle-series submetric is a composite sum value based on at least two of the plurality of electrical signals at peak times during the at least two cardiac cycles, wherein the sum amplitude metric is the single-cycle submetric divided by the cycle-series submetric.

7. The system of claim 1, wherein the at least one metric for each cardiac cycle comprises an interval metric, wherein the single-cycle submetric is a time interval between a peak time of the cardiac cycle and a peak time of a previous or following cardiac cycle of the plurality of cardiac cycles, wherein the cycle-series submetric is a composite interval value based on all time intervals between peak times of at least two cardiac cycles.

8. The system of claim 1, wherein the at least one metric for each cardiac cycle comprises a regional electrode contact metric, wherein the regional electrode contact metric is representative of an amount of the plurality of electrodes located proximate a selected region of the patient that captured a valid electrocardiographic signal from the tissue in the selection region of the patient during the cardiac cycle.

9. The system of claim 1, wherein selecting a cardiac cycle of the plurality of cardiac cycles based on the at least one metric comprises:
comparing the at least one metric for each cardiac cycle to at least one threshold value to assign a score the cardiac cycle.

10. The system of claim 1, wherein selecting a cardiac cycle of the plurality of cardiac cycles based on the at least one metric comprises:
assigning a score to each cardiac cycle of the plurality of cardiac cycles based on the at least one metric; and
selecting the cardiac cycle of the plurality of cardiac cycles having the best score.

11. The system of claim 1, wherein selecting a cardiac cycle of the plurality of cardiac cycles based on the at least one metric comprises:
assigning a score to each cardiac cycle of the plurality of cardiac cycles based on the at least one metric; and
removing from consideration of selection cardiac cycles of the plurality of cardiac cycles having a score greater than a scoring threshold value.

12. The system of claim 11, wherein selecting a cardiac cycle of the plurality of cardiac cycles based on the at least one metric comprises removing from consideration of selection cardiac cycles of the plurality of cardiac cycles following or preceding cardiac cycles having a score greater than the scoring threshold value.

13. The system of claim 1, wherein selecting a cardiac cycle of the plurality of cardiac cycles based on the at least one metric comprises removing from consideration of selection the cardiac cycle that occurs last if at least two cardiac cycles remain being considered for selection.

14. The system of claim 1, wherein the computing apparatus is further configured to execute generating electrical activation times based on the plurality of cardiac signals of the selected cardiac cycle.

15. A method for use in cardiac evaluation comprising:
monitoring electrical activity from tissue of a patient using a plurality of electrodes to generate a plurality of electrical signals over a plurality of cardiac cycles;
generating at least one metric for each cardiac cycle based on a single-cycle submetric and a cycle-series submetric, wherein the single-cycle submetric is based on at least two of the plurality of electrical signals during the cardiac cycle and the cycle-series submetric is based on at least two of the plurality of electrical signals during at least two cardiac cycles, wherein the at least one metric for each cardiac cycle comprises an electrode contact metric, wherein the electrode contact metric is representative of an amount of the plurality of electrodes that captured a valid electrocardiographic signal from the tissue of the patient during the cardiac cycle; and
selecting a cardiac cycle of the plurality of cardiac cycles based on the at least one metric.

16. The method of claim 15, wherein the single-cycle submetric is a value generated from at least two of the plurality of electrical signals at a peak time during the cardiac cycle and the cycle-series submetric is a value generated from at least two electrical signals of the plurality of electrical signals at peak times during the at least two cardiac cycles.

17. The method of claim 15, wherein the at least one metric for each cardiac cycle comprises a maximum amplitude metric, wherein the single-cycle submetric is a maximum value across at least two of the plurality electrical signals at a peak time during cardiac cycle, wherein the cycle-series submetric is a composite maximum value based on all of the maximum values of at least two of the plurality of electrical signals at peak times during the at least two cardiac cycles, wherein the maximum amplitude metric is the single-cycle submetric divided by the cycle-series submetric.

18. The method of claim 17, wherein the composite maximum value is the median of the maximum values of the at least two of the plurality of electrical signals at the peak times during the at least two cardiac cycles.

19. The method of claim 15, wherein the at least one metric for each cardiac cycle comprises a minimum amplitude metric, wherein the single-cycle submetric is a minimum value across at least two of the plurality electrical signals at a peak time during cardiac cycle, wherein the cycle-series submetric is a composite minimum value based on all of the minimum values of at least two of the plurality of electrical signals at peak times during the at least two cardiac cycles, wherein the minimum amplitude metric is the single-cycle submetric divided by the cycle-series submetric.

20. The method of claim 15, wherein the at least one metric for each cardiac cycle comprises a sum amplitude metric, wherein the single-cycle submetric is a sum of at least two of the plurality of electrical signals at a peak time during the cardiac cycle, wherein the cycle-series submetric is a composite sum value based on at least two of the plurality of electrical signals at peak times during the at least two cardiac cycles, wherein the sum amplitude metric is the single-cycle submetric divided by the cycle-series submetric.

21. The method of claim 15, wherein the at least one metric for each cardiac cycle comprises an interval metric, wherein the single-cycle submetric is a time interval between a peak time of the cardiac cycle and a peak time of a previous or following cardiac cycle of the plurality of cardiac cycles, wherein the cycle-series submetric is a composite interval value based on all time intervals between peak times of at least two cardiac cycles.

22. The method of claim 15, wherein the at least one metric for each cardiac cycle comprises a regional electrode contact metric, wherein the regional electrode contact metric is representative of an amount of the plurality of electrodes located proximate a selected region of the patient that captured a valid electrocardiographic signal from the tissue in the selection region of the patient during the cardiac cycle.

23. The method of claim 15, wherein selecting a cardiac cycle of the plurality of cardiac cycles based on the at least one metric comprises:
comparing the at least one metric for each cardiac cycle to at least one threshold value to assign a score the cardiac cycle.

24. The method of claim 15, wherein selecting a cardiac cycle of the plurality of cardiac cycles based on the at least one metric comprises:
assigning a score to each cardiac cycle of the plurality of cardiac cycles based on the at least one metric; and
selecting the cardiac cycle of the plurality of cardiac cycles having the best score.

25. The method of claim 15, wherein selecting a cardiac cycle of the plurality of cardiac cycles based on the at least one metric comprises:
assigning a score to each cardiac cycle of the plurality of cardiac cycles based on the at least one metric; and
removing from consideration of selection cardiac cycles of the plurality of cardiac cycles having a score greater than a scoring threshold value.

26. The method of claim 25, wherein selecting a cardiac cycle of the plurality of cardiac cycles based on the at least one metric comprises removing from consideration of selection cardiac cycles of the plurality of cardiac cycles following or preceding cardiac cycles having a score greater than the scoring threshold value.

27. The method of claim 15, wherein selecting a cardiac cycle of the plurality of cardiac cycles based on the at least one metric comprises removing from consideration of selection the cardiac cycle that occurs last if at least two cardiac cycles remain being considered for selection.

28. The method of claim 15, wherein the method further comprises generating electrical activation times based on the plurality of cardiac signals of the selected cardiac cycle.

29. A method for use in cardiac evaluation comprising:
monitoring electrical activity from tissue of a patient using a plurality of electrodes to generate a plurality of electrical signals over a plurality of cardiac cycles;
generating at least one metric for each cardiac cycle based on a single-cycle submetric and a cycle-series submetric, wherein the single-cycle submetric is based on at least two of the plurality of electrical signals during the cardiac cycle and the cycle-series submetric is based on at least two of the plurality of electrical signals during at least two cardiac cycles; and
selecting a cardiac cycle of the plurality of cardiac cycles based on the at least one metric, wherein selecting a cardiac cycle of the plurality of cardiac cycles based on the at least one metric comprises:
assigning a score to each cardiac cycle of the plurality of cardiac cycles based on the at least one metric;
removing from consideration of selection cardiac cycles of the plurality of cardiac cycles having a score greater than a scoring threshold value; and
removing from consideration of selection cardiac cycles of the plurality of cardiac cycles following or preceding cardiac cycles having a score greater than the scoring threshold value.

30. The method of claim 29, wherein selecting a cardiac cycle of the plurality of cardiac cycles based on the at least one metric comprises removing from consideration of selection the cardiac cycle that occurs last if at least two cardiac cycles remain being considered for selection.

31. The method of claim 29, wherein the method further comprises generating electrical activation times based on the plurality of cardiac signals of the selected cardiac cycle.

* * * * *